United States Patent
Cheng et al.

(10) Patent No.: US 11,864,811 B2
(45) Date of Patent: Jan. 9, 2024

(54) SYSTEM AND METHOD FOR ABLATING BREAST CANCER CELLS WITH COLD PLASMA

(71) Applicant: Jerome Canady Research Institute for Advanced Biological and Technological Sciences, Takoma Park, MD (US)

(72) Inventors: Xiaoqian Cheng, Falls Church, VA (US); Jerome Canady, Lakeland, FL (US); Warren J Rowe, Hyattsville, MD (US)

(73) Assignee: US Patent Innovations, LLC, Takoma Park, MD (US)

( * ) Notice: Subject to any disclaimer, the term of this patent is extended or adjusted under 35 U.S.C. 154(b) by 1051 days.

(21) Appl. No.: 16/547,962

(22) Filed: Aug. 22, 2019

(65) Prior Publication Data

US 2020/0060748 A1     Feb. 27, 2020

Related U.S. Application Data

(60) Provisional application No. 62/721,265, filed on Aug. 22, 2018.

(51) Int. Cl.
*A61B 18/14* (2006.01)
*A61B 18/04* (2006.01)
*A61B 18/00* (2006.01)

(52) U.S. Cl.
CPC .. *A61B 18/042* (2013.01); *A61B 2018/00333* (2013.01); *A61B 2018/00583* (2013.01); *A61B 2018/00589* (2013.01)

(58) Field of Classification Search
CPC .............. A61B 18/042; A61B 18/1206; A61B 2018/00333; A61B 2018/00577;
(Continued)

(56) References Cited

U.S. PATENT DOCUMENTS 9,999,462 B2    6/2018 Canady et al.
10,023,858 B2   7/2018 Canady et al.
(Continued)

FOREIGN PATENT DOCUMENTS

WO    2018/191265 A1    10/2018

OTHER PUBLICATIONS

Wang, Mian; "Cold Atmospheric Plasma for Selectively Ablating Metastatic Breast Cancer Cells"; Sep. 11, 2013; PLOSONE; vol. 8, Issue 9; pp. 1-11. (Year: 2013).*
(Continued)

*Primary Examiner* — Michael F Peffley
*Assistant Examiner* — Amanda L Zink
(74) *Attorney, Agent, or Firm* — 24IP LAW GROUP USA, PLLC; Timothy DeWitt

(57) ABSTRACT

A method for performing cold atmospheric plasma therapy to treat breast cancer. The cancerous tumor is sampled and cold atmospheric plasma treatment is performed on sampled cancerous tumor cells ex vivo. The results of the testing are stored in an electronic storage media. A cell viability reduction rate of said tested samples is calculated with a processor and stored in memory. An average cell viability reduction rate is then calculated by the processor for the cancerous tumor. Cold atmospheric plasma dosages to be used in treatment of the cancerous tumor in vivo are then projected using the processor. The tumor is surgically removed from the patient. The surgical margins of the tumor are then treated with cold atmospheric plasma at the projected dosages.

2 Claims, 21 Drawing Sheets

(58) Field of Classification Search
CPC .......... A61B 2018/00583; A61B 2018/00589; A61B 2018/00791; A61B 2090/376; A61B 2090/378

See application file for complete search history.

(56) References Cited

U.S. PATENT DOCUMENTS

| | | | |
|---|---|---|---|
| 10,213,614 | B2 | 2/2019 | Keidar et al. |
| 10,329,535 | B2 | 6/2019 | Trink et al. |
| 10,405,913 | B2 | 9/2019 | Canady et al. |
| 10,772,671 | B2* | 9/2020 | Chen .................. A61K 41/00 |
| 2014/0378892 | A1* | 12/2014 | Keidar ................ A61B 18/042 604/23 |
| 2017/0183631 | A1 | 6/2017 | Keidar et al. |
| 2017/0354453 | A1* | 12/2017 | Krasik ................ A61B 18/042 |
| 2018/0271579 | A1 | 9/2018 | Keidar et al. |
| 2022/0133595 | A1* | 5/2022 | Miksztal ............. A61K 31/445 604/403 |

OTHER PUBLICATIONS

DeSantis, C.E.; Ma, J.; Goding Sauer, A.; Newman, L.A.; Jemal, A. Breast cancer statistics, 2017, racial disparity in mortality by state. CA Cancer J Clin 2017, 67, 439-448.

Wahba, H.A.; El-Hadaad, H.A. Current approaches in treatment of triple-negative breast cancer. Cancer Biol Med 2015, 12, 106-116.

Foulkes, W.D.; Smith, I.E.; Reis-Filho, J.S. Triple-negative breast cancer. The New England Journal of Medicine 2010, 363, 1938-1948.

Liedtke, C.; Mazouni, C.; Hess, K.R.; Andre, F.; Tordai, A.; Mejia, J.A.; Symmans, W.F.; Gonzalez-Angulo, A.M.; Hennessy, B.; Green, M., et al. Response to neoadjuvant therapy and long-term survival in patients with triplenegative breast cancer. J Clin Oncol 2008, 26, 1275-1281.

Niemira, B.A.; Boyd, G.; Sites, J. Cold plasma rapid decontamination of food contact surfaces contaminated with salmonella biofilms. J Food Sci 2014, 79, M917-922.

Schmidt, A.; Woedtke, T.V.; Stenzel, J.; Lindner, T.; Polei, S.; Vollmar, B.; Bekeschus, S. One year follow-up risk assessment in skh-1 mice and wounds treated with an argon plasma jet. Int J Mol Sci 2017, 18.

Pierdzioch, P.; Hartwig, S.; Herbst, S.R.; Raguse, J.D.; Dommisch, H.; Abu-Sirhan, S.; Wirtz, H.C.; Hertel, M.; Paris, S.; Preissner, S. Cold plasma: A novel approach to treat infected dentin-a combined ex vivo and in vitro study. Clin Oral Investig 2016, 20, 2429-2435.

Wu, Y.; Liang, Y.; Wei, K.; Li, W.; Yao, M.; Zhang, J. Rapid allergen inactivation using atmospheric pressure cold plasma. Environ Sci Technol 2014, 48, 2901-2909.

Volotskova, O.; Dubrovsky, L.; Keidar, M.; Bukrinsky, M. Cold atmospheric plasma inhibits hiv-1 replication in macrophages by targeting both the virus and the cells. PLoS One 2016, 11, e0165322.

Yan, D.; Sherman, J.H.; Keidar, M. Cold atmospheric plasma, a novel promising anti-cancer treatment modality. Oncotarget 2017, 8, 15977-15995.

Keidar, M. Plasma for cancer treatment. Plasma Sources Science and Technology 2015, 24.

Laroussi, M.; Lu, X.; Keidar, M. Perspective: The physics, diagnostics, and applications of atmospheric pressure low temperature plasma sources used in plasma medicine. Journal of Applied Physics 2017, 122.

Ishaq, M.; Han, Z.J.; Kumar, S.; Evans, M.D.M.; Ostrikov, K.K. Atmosphericpressure plasma-and trail-induced apoptosis in trail-resistant colorectal cancer cells. Plasma Processes and Polymers 2015, 12, 574-582.

Adachi, T.; Tanaka, H.; Nonomura, S.; Hara, H.; Kondo, S.; Hori, M. Plasmaactivated medium induces a549 cell injury via a spiral apoptotic cascade involving the mitochondrial-nuclear network. Free Radic Biol Med 2015, 79, 28-44.

Weiss, M.; Gumbel, D.; Hanschmann, E.M.; Mandelkow, R.; Gelbrich, N.; Zimmermann, U.; Walther, R.; Ekkernkamp, A.; Sckell, A.; Kramer, A., et al. Cold atmospheric plasma treatment induces anti-proliferative effects in prostate cancer cells by redox and apoptotic signaling pathways. PLoS One 2015, 10, e0130350.

Shi, X.-M.; Zhang, G.-J.; Chang, Z.-S.; Wu, X.-L.; Liao, W.-L.; Li, N. Viability reduction of melanoma cells by plasma jet via inducing g1/s and g2/m cell cycle arrest and cell apoptosis. IEEE Transactions on Plasma Science 2014, 42, 1640-1647.

Gherardi, M.; Turrini, E.; Laurita, R.; De Gianni, E.; Ferruzzi, L.; Liguori, A.; Stancampiano, A.; Colombo, V.; Fimognari, C. Atmospheric non-equilibrium plasma promotes cell death and cell-cycle arrest in a lymphoma cell line. Plasma Processes and Polymers 2015, 12, 1354-1363.

Volotskova, O.; Hawley, T.S.; Stepp, M.A.; Keidar, M. Targeting the cancer cell cycle by cold atmospheric plasma. Sci Rep 2012, 2, 636.

Ruwan Kumara, M.H.; Piao, M.J.; Kang, K.A.; Ryu, Y.S.; Park, J.E.; Shilnikova, K.; Jo, J.O.; Mok, Y.S.; Shin, J.H.; Park, Y., et al. Non-thermal gas plasmainduced endoplasmic reticulum stress mediates apoptosis in human colon cancer cells. Oncol Rep 2016, 36, 2268-2274.

Zhao, S.; Xiong, Z.; Mao, X.; Meng, D.; Lei, Q.; Li, Y.; Deng, P.; Chen, M.; Tu, M.; Lu, X., et al. Atmospheric pressure room temperature plasma jets facilitate oxidative and nitrative stress and lead to endoplasmic reticulum stress dependent apoptosis in hepg2 cells. PLoS One 2013, 8, e73665.

Zhang, X.; Zhang, C.; Zhou, Q.Q.; Zhang, X.F.; Wang, L.Y.; Chang, H.B.; Li, H P.; Oda, Y.; Xing, X.H. Quantitative evaluation of DNA damage and mutation rate by atmospheric and room-temperature plasma (artp) and conventional mutagenesis. Appl Microbiol Biotechnol 2015, 99, 5639-5646.

Chung, W.H. Mechanisms of a novel anticancer therapeutic strategy involving atmospheric pressure plasma-mediated apoptosis and DNA strand break formation. Arch Pharm Res 2016, 39, 1-9.

Chang, J.W.; Kang, S.U.; Shin, Y.S.; Kim, K.I.; Seo, S.J.; Yang, S.S.; Lee, J.S.; Moon, E.; Baek, S.J.; Lee, K., et al. Non-thermal atmospheric pressure plasma induces apoptosis in oral cavity squamous cell carcinoma: Involvement of DNAdamage-triggering sub-g(1) arrest via the atm/p53 pathway. Arch Biochem Biophys 2014, 545, 133-140.

Weltmann, K.D.; Kindel, E.; von Woedtke, T.; Hahnel, M.; Stieber, M.; Brandenburg, R. Atmospheric-pressure plasma sources: Prospective tools for plasma medicine. Pure and Applied Chemistry 2010, 82, 1223-1237.

Yan, D.; Talbot, A.; Nourmohammadi, N.; Cheng, X.; Canady, J.; Sherman, J.; Keidar, M. Principles of using cold atmospheric plasma stimulated media for cancer treatment. Sci Rep 2015, 5, 18339.

Xu, X.; Dai, X.; Xiang, L.; Cai, D.; Xiao, S.; Ostrikov, K. Quantitative assessment of cold atmospheric plasma anti-cancer efficacy in triple-negative breast cancers. Plasma Processes and Polymers 2018.

* cited by examiner

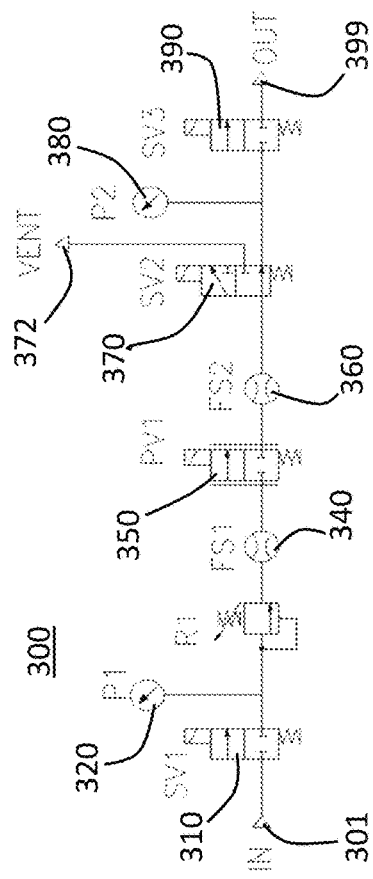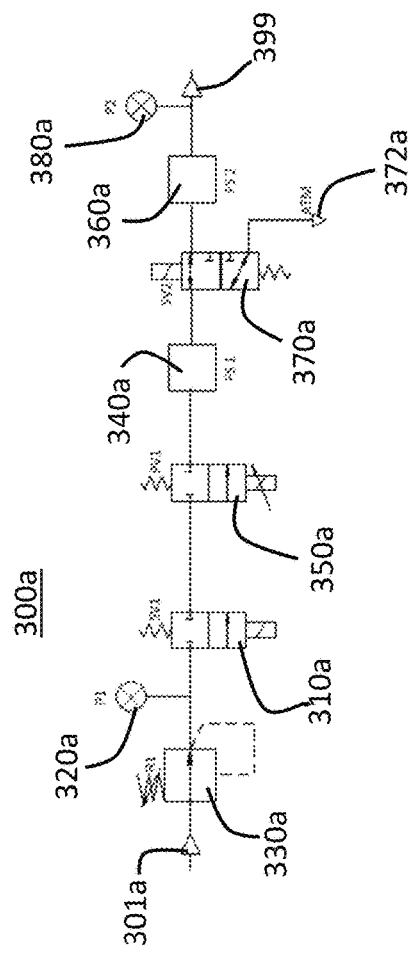
FIG. 3A
FIG. 3B

SYSTEM AND METHOD FOR ABLATING BREAST CANCER CELLS WITH COLD PLASMA

CROSS-REFERENCE TO RELATED APPLICATIONS

The present application claims the benefit of the filing date of U.S. Provisional Patent Application Ser. No. 62/721,265 filed by the present inventors on Aug. 22, 2018.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to systems and methods for treatment of cancer with cold atmospheric plasma.

Brief Description of the Related Art

Breast cancer is the most common cancer diagnosed among US women (excluding skin cancers) and is the second leading cause of cancer death among women after lung cancer. See, C. E. DeSantis, J. Ma, A. Goding Sauer, L. A. Newman, A. Jemal, "Breast cancer statistics, 2017, racial disparity in mortality by state," CA Cancer J Clin 2017, 67, 439-448. Triple-negative breast cancer refers to the breast cancer phenotype which has an absence or low level expression of estrogen, progesterone, and HER2 receptors. See, H. A. Wahba, H. A. El-Hadaad, "Current approaches in treatment of triple-negative breast cancer," Cancer Biol Med 2015, 12, 106-116. It is known for its poor clinical outcome and lack of effective targeted therapy because women with triple-negative breast cancer do not benefit from endocrine therapy or trastuzumab. Chemotherapy is currently the mainstay of systemic medical treatment. See, W. D. Foulkes, I. E. Smith, J. S. Reis-Filho, "Triple-negative breast cancer," The New England Journal of Medicine 2010, 363, 1938-1948. Patients with triple-negative disease have a lower 3-year survival rate following chemotherapy than patients with breast cancers of other subtypes. See, Liedtke, et al., "Response to neoadjuvant therapy and long-term survival in patients with triple-negative breast cancer," J Clin Oncol 2008, 26, 1275-1281.

Cold atmospheric plasma (CAP) has been extensively studied for its biomedical use in various fields such as surface decontamination, wound healing, dental treatment, allergen destruction, HIV virus treatment, among others. In particular, the research of CAP as a potential oncotherapeutic approach has thrived over the past decade and the mechanism is being increasingly understood. Keidar, M. Plasma for cancer treatment. Plasma Sources Science and Technology 2015, 24 and M. Laroussi, X. Lu, and M. Keidar, "Perspective: The physics, diagnostics, and applications of atmospheric pressure low temperature plasma sources used in plasma medicine," Journal of Applied Physics 2017, 122. It is widely reported that CAP deactivated more than 20 types of cancer in vitro by inducing apoptosis cell cycle arrest, endoplasmic reticulum stress and DNA damage. See, Ishaq, et al., "Atmospheric-pressure plasma- and trail-induced apoptosis in trail-resistant colorectal cancer cells," Plasma Processes and Polymers 2015, 12, 574-582; Adachi, et al., "Plasma-activated medium induces a549 cell injury via a spiral apoptotic cascade involving the mitochondrial-nuclear network," Free Radic Biol Med 2015, 79, 28-44; Weiss, et al., "Cold atmospheric plasma treatment induces anti-proliferative effects in prostate cancer cells by redox and apoptotic signaling pathways," PLoS One 2015, 10, e0130350; Shi, et al., "Viability reduction of melanoma cells by plasma jet via inducing g1/s and g2/m cell cycle arrest and cell apoptosis," IEEE Transactions on Plasma Science 2014, 42, 1640-1647; Gherardi, et al., "Atmospheric non-equilibrium plasma promotes cell death and cell-cycle arrest in a lymphoma cell line," Plasma Processes and Polymers 2015, 12, 1354-1363; Volotskova, et al., "Targeting the cancer cell cycle by cold atmospheric plasma," Sci Rep 2012, 2, 636; Ruwan Kumara, et al., "Non-thermal gas plasma-induced endoplasmic reticulum stress mediates apoptosis in human colon cancer cells," Oncol Rep 2016, 36, 2268-2274; Zhao, S., et al., "Atmospheric pressure room temperature plasma jets facilitate oxidative and nitrative stress and lead to endoplasmic reticulum stress dependent apoptosis in hepg2 cells," PLoS One 2013, 8, e73665; Zhang, et al., "Quantitative evaluation of DNA damage and mutation rate by atmospheric and room-temperature plasma (artp) and conventional mutagenesis," Appl Microbiol Biotechnol 2015, 99, 5639-5646; W. H. Chung, "Mechanisms of a novel anticancer therapeutic strategy involving atmospheric pressure plasma-mediated apoptosis and DNA strand break formation," Arch Pharm Res 2016, 39, 1-9; and Chang, et al., "Non-thermal atmospheric pressure plasma induces apoptosis in oral cavity squamous cell carcinoma: Involvement of DNA-damage-triggering sub-g(1) arrest via the atm/p53 pathway. Arch Biochem Biophys 2014, 545, 133-140.

Several different systems and methods for performing Cold Atmospheric Plasma (CAP) treatment have been disclosed. For example, U.S. Published Patent Application No. 2014/0378892 discloses a two-electrode system for CAP treatement. U.S. Pat. No. 9,999,462 discloses a converter unit for using a traditional electrosurgical system with a single electrode CAP accessory to perform CAP treatment.

SUMMARY OF THE INVENTION

In a preferred embodiment, the present invention is a system and method for performing cold atmospheric plasma treatment on breast cancer. Viability of the cancer cells was effectively reduced in a time- and power-dependent manner. The present invention allows for the treatment of surgical margins following the removal of a tumor and for ablating cancer cells using a single device and provides dosage estimations for patients in clinical applications. Triple negative breast cancer is a phenotype of breast cancer where the expression level of estrogen, progesterone and HER2 receptors are low or absent. It is more frequently diagnosed in younger and premenopausal women, among which African and Hispanic have a higher rate. The unit effectively reduced the viability of triple negative breast cancer up to 80% without thermal damage.

In another preferred embodiment, the present invention is a method for performing cold atmospheric plasma therapy to treat breast cancer. The cancerous tumor is sampled and cold atmospheric plasma treatment is performed on sampled cancerous tumor cells ex vivo. The results of the testing are stored in an electronic storage media. A cell viability reduction rate of said tested samples is calculated with a processor and stored in memory. An average cell viability reduction rate is then calculated by the processor for the cancerous tumor. Cold atmospheric plasma dosages to be used in treatment of the cancerous tumor in vivo are then projected using the processor. The tumor is surgically removed from the patient. The surgical margins of the tumor are then treated with cold atmospheric plasma at the projected dosages.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIG. 3A is a schematic flow diagram illustrating the gas flow through the module and the method by which the module controls the gas flow in accordance with a preferred embodiment of the present invention.

FIG. 3B is a schematic flow diagram illustrating the gas flow through an alternate embodiment of the module and the method by which the module controls the gas flow in accordance with a preferred embodiment of the present invention.

FIG. 8A is a group of thermal images of CAP-treated media. FIG. 8B is a graph of temperature of CAP-treated media as a function of treatment time. FIG. 8C is a graph of temperature of the CAP beam.

FIG. 9A is a group of thermal images of CAP-treated media. FIG. 9B is a graph of temperature of CAP-treated media as a function of treatment time. FIG. 9C is a graph of temperature of the CAP beam.

In FIG. 10A cells were treated by CAP at 3 lpm in 12-well plates. In FIG. 10B cells were treated by CAP at 1 lpm in 96-well plates.

DETAILED DESCRIPTION OF THE PREFERRED EMBODIMENTS

The present invention will be described with reference to the drawings. The methods are performed using a cold atmospheric plasma system in which energy from a high frequency electrosurgical unit is converted to low frequency energy. An systems are disclosed in U.S. Published Patent Application No. 2018/0271582, filed on May 29, 2018, which is hereby incorporated by reference in its entirety.

Figure 12:
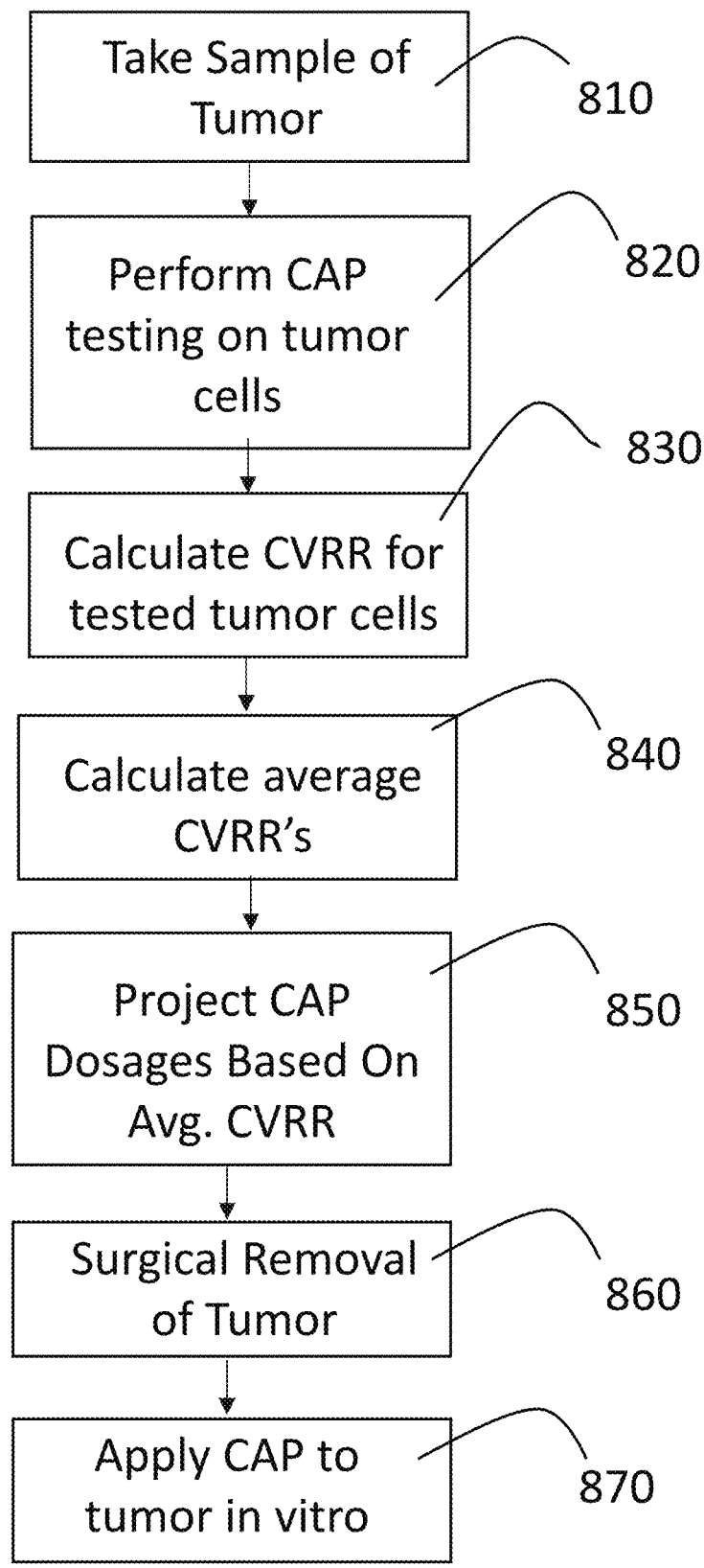
FIG. 12 is a flow chart for performing a cold atmospheric plasma treatment of cancer cells in accordance with a preferred embodiment of the present invention.

Thus, as shown in FIG. 12, a method can be performed in which cold atmospheric plasma treatment of cancer cells is performed. The tumor is sampled (810). CAP is performed on the tumor using a CAP system. 820. A Cell Viability Reduction Rate (CVRR) (described below) is calculated 830 for the tested tumor cells. An average CVRR is calculated for the tumor cells 840. CAP doses for treatment of the tumor are projected based upon the calculated average CVRR 850. The tumor is surgically removed 860 and CAP is performed on the boundaries of the removal area using the projected CAP settings. 870.

A preferred embodiment of a CAP enabled generator is described with reference to the drawings. A gas-enhanced electrosurgical generator 100 in accordance with a preferred embodiment of the present invention is shown in FIGS. 1A-1G. The gas-enhanced generator has a housing 110 made of a sturdy material such as plastic or metal similar to materials used for housings of conventional electrosurgical generators. The housing 110 has a removable cover 114. The housing 110 and cover 114 have means, such as screws 119, tongue and groove, or other structure for removably securing the cover to the housing. The cover 114 may comprise just the top of the housing or multiple sides, such as the top, right side and left side, of the housing 110. The housing 110 may have a plurality of feet or legs 140 attached to the bottom of the housing. The bottom 116 of the housing 110 may have a plurality of vents 118 for venting from the interior of the gas-enhanced generator.

On the face 112 of the housing 114 there is a touch-screen display 120 and a plurality of connectors 132, 134 for connecting various accessories to the generator, such as an argon plasma probe, a hybrid plasma probe, a cold atmospheric plasma probe, or any other electrosurgical attachment. There is a gas connector 136 for connecting, for example, a $CO_2$ supply for insufflating an abdomen. The face 112 of the housing 110 is at an angle other than 90 degrees with respect to the top and bottom of the housing 110 to provide for easier viewing and use of the touch screen display 120 by a user.

Figure 1A:
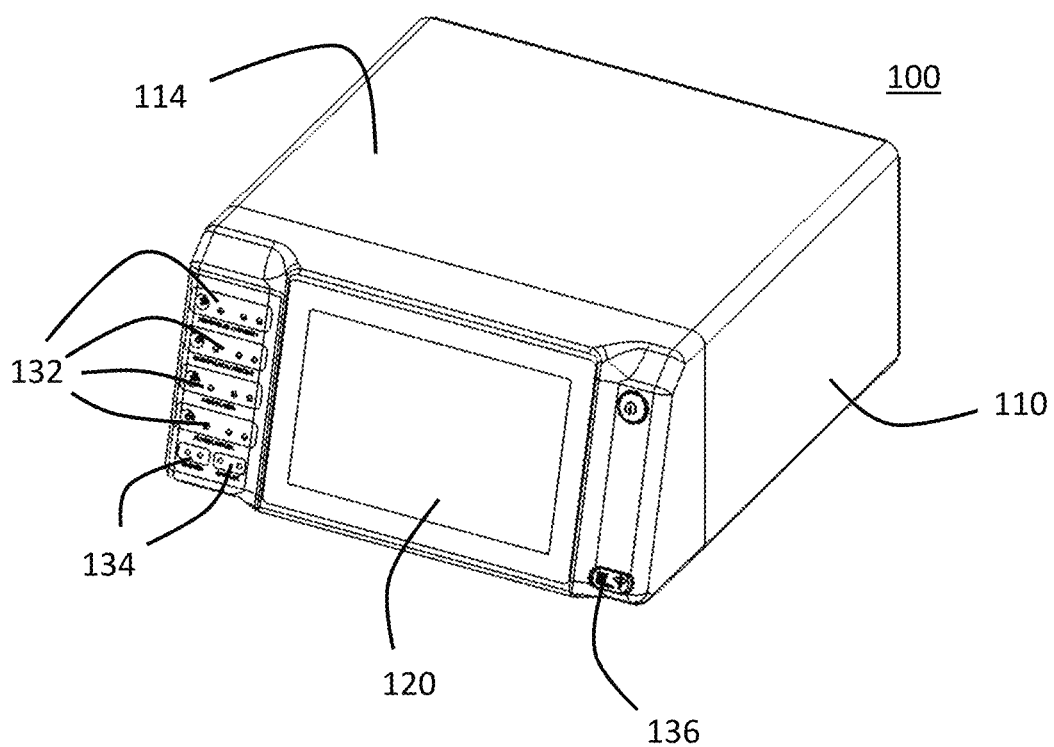
FIG. 1A is a perspective view of a preferred embodiment of a gas-enhanced electrosurgical generator.
Figure 1B:
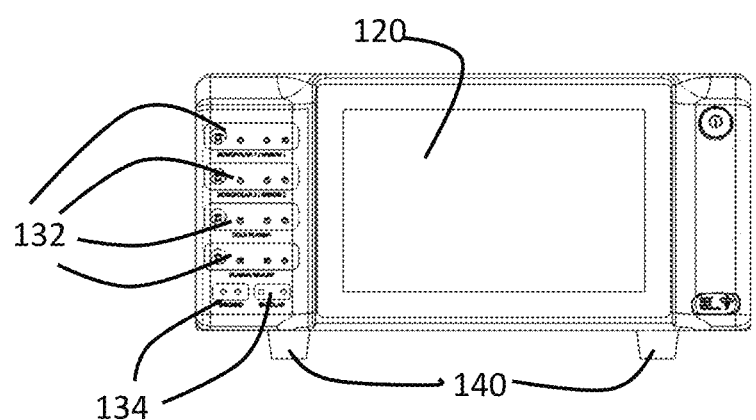
FIG. 1B is a front view of a preferred embodiment of a gas-enhanced electrosurgical generator.
Figure 1C:
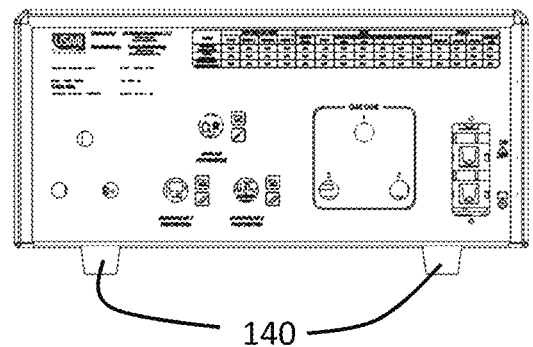
FIG. 1C is a rear view of a preferred embodiment of a gas-enhanced electrosurgical generator.
Figure 1D:
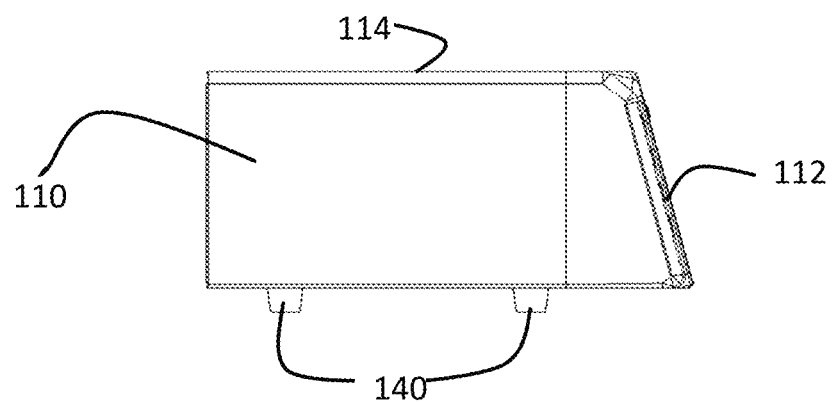
FIG. 1D is a left side view of a preferred embodiment of a gas-enhanced electrosurgical generator.
Figure 1E:
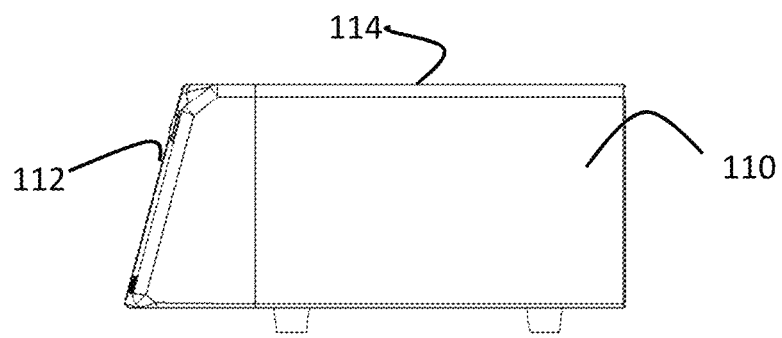
FIG. 1E is a right view of a preferred embodiment of a gas-enhanced electrosurgical generator.
Figure 1F:
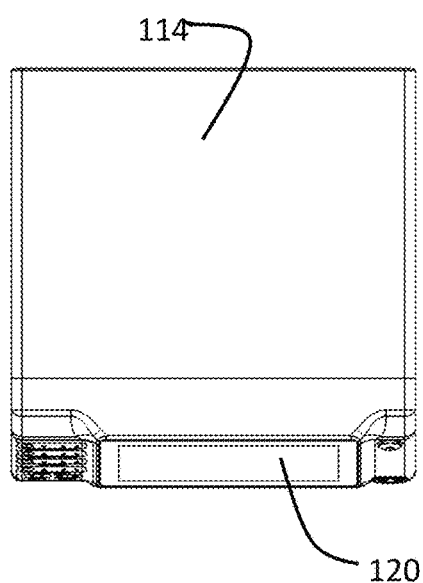
FIG. 1F is a top view of a preferred embodiment of a gas-enhanced electrosurgical generator.
Figure 1G:
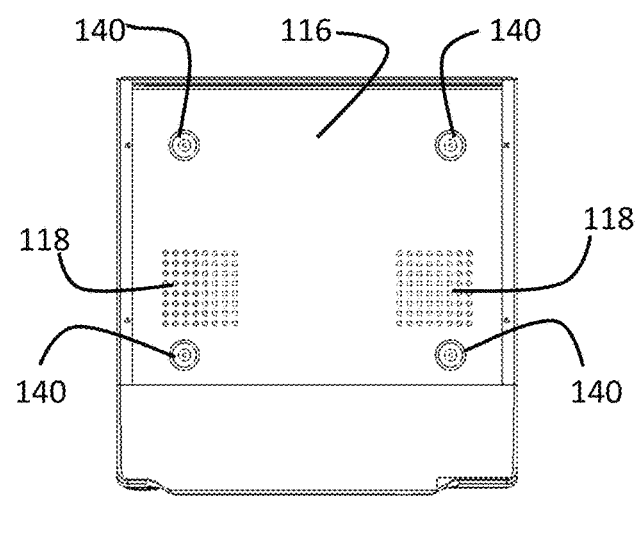
FIG. 1G is a bottom view of a preferred embodiment of a gas-enhanced electrosurgical generator.
Figure 2A:
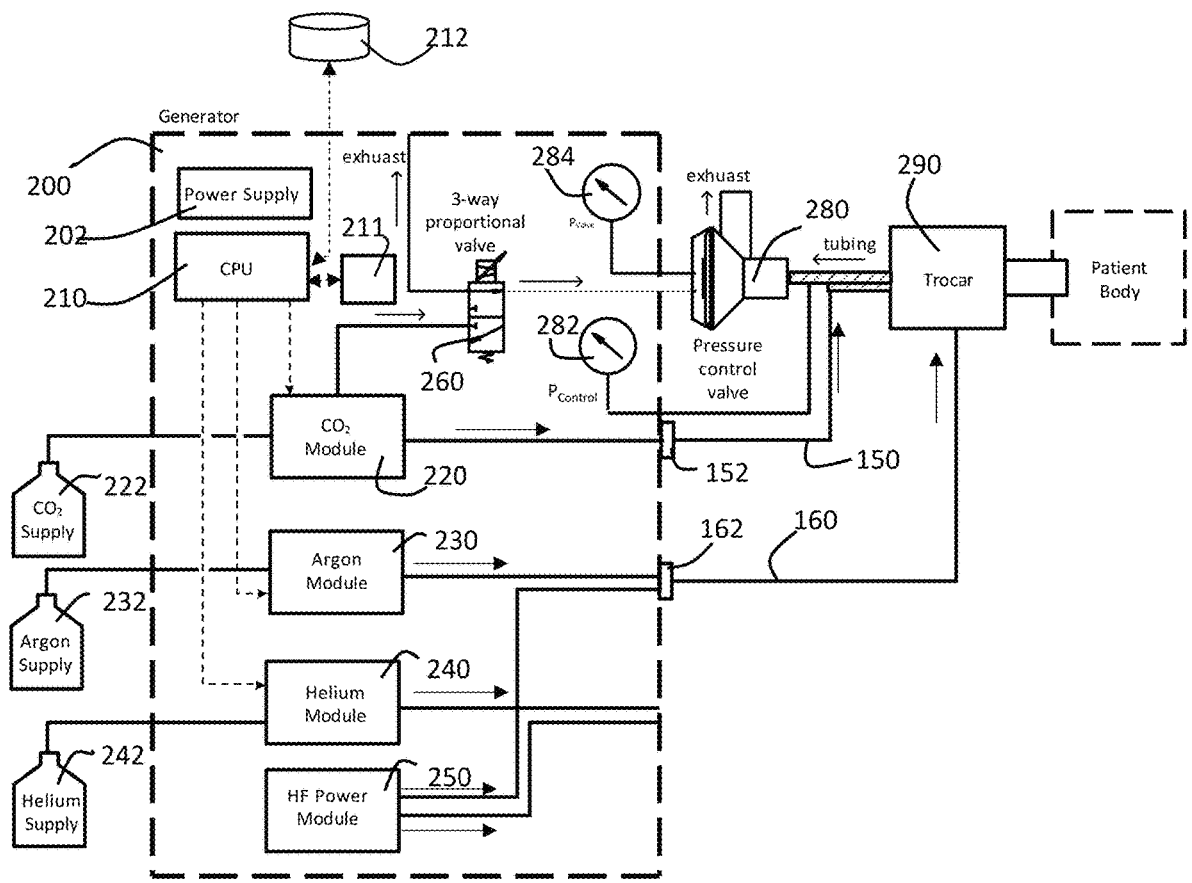
FIG. 2A is a block diagram of a preferred embodiment of pressure control system of a gas-enhanced electrosurgical generator in accordance with the present invention configured to perform an argon-enhanced electrosurgical procedure.

One or more of the gas control modules may be mounting within a gas-enhanced electrosurgical generator 100. A gas pressure control system 200 for controlling a plurality of gas control modules 220, 230, 240 within a gas-enhanced electrosurgical generator is described with reference to FIGS. 2A-2D. A plurality of gas supplies 222, 232, 242 are connected to the gas pressure control system 200, and more specifically, to the respective gas control modules 220, 230, 240 within the gas pressure control system 200. The gas pressure control system 200 has a power supply 202 for supplying power to the various components of the system. A CPU 210 controls the gas pressure control modules 220, 230, 240 in accordance with settings or instructions entered into the system through a graphical user interface on the display 120. The system is shown with gas control modules for $CO_2$, argon and helium, but the system is not limited to those particular gases. In the embodiment shown in FIGS. 2A-2D, the $CO_2$ is shown as the gas used to insufflate an abdomen (or other area of a patient). The gas pressure control system 200 has a 3-way proportional valve connected to the gas control module 220. While FIG. 2A shows the 3-way proportional valve connected only to the CO2 control module 220, the 3-way proportional valves could be connected to a different gas control module 230 or 240. The gas pressure control system 200 further has an HF power module 250 for supplying high frequency electrical energy for various types of electrosurgical procedures. The HF power module contains conventional electronics such as are known for provide HF power in electrosurgical generators. Exemplary systems include, but are not limited to, those disclosed in U.S. Pat. Nos. 4,040,426 and 4,781,175. The system further could have a converter unit for converting the HF power to a lower frequency, such as may be used for cold atmospheric plasma and is described in U.S. Patent Application Publication No. 2015/0342663.

The outlet port of gas control module 220 is connected to a connector 136 on the generator housing. While connector 136 and the other connectors are shown on the front face of the housing 110, they could be elsewhere on the housing.

Figure 2B:
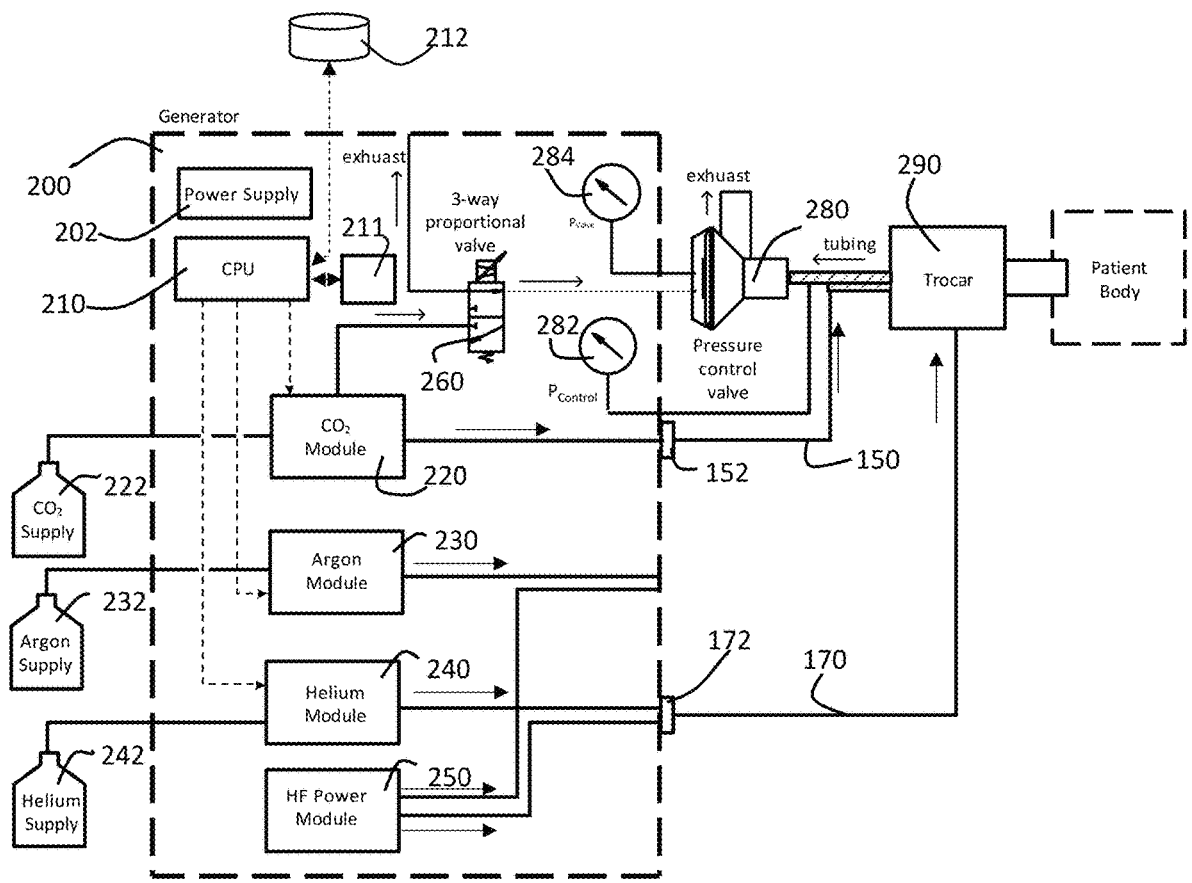
FIG. 2B is a block diagram of a preferred embodiment of pressure control system of a gas-enhanced electrosurgical generator in accordance with the present invention configured to perform a cold atmospheric plasma procedure.
Figure 2C:
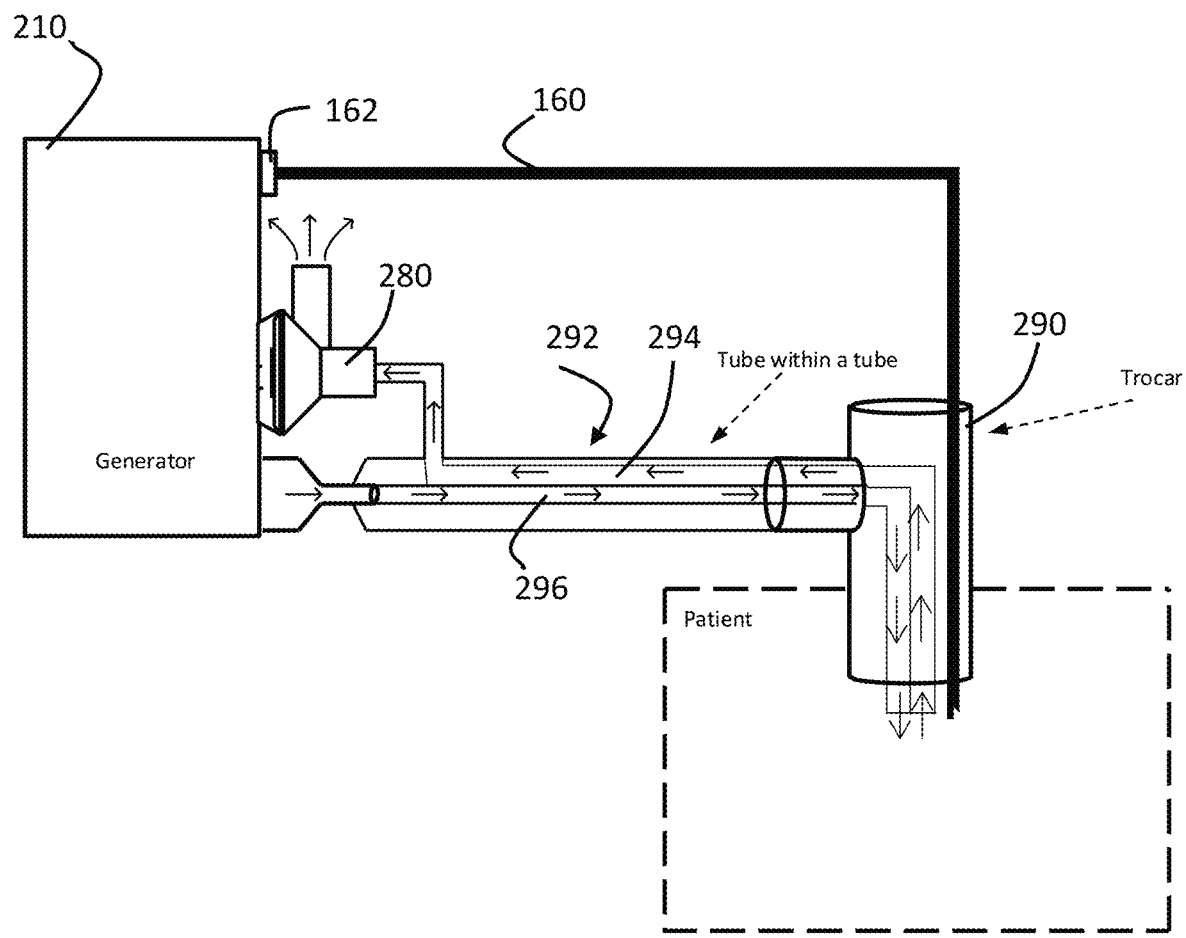
FIG. 2C is a diagram of a trocar for the embodiment of FIG. 2A in accordance with the present invention.

The outlet ports of gas control modules 230, 240 each are connected to tubing or other channel to a connector 132. A connector 152 connects to connector 136 and is as tubing that runs to and connects to tubing 292. The tubing 292 is connected to a pressure control valve or stopcock 280 and extends into the trocar. The pressure control valve 280 is used to control pressure within the patient. The gas pressure control system further has a pressure sensor 282 connected to the tubing 292 to sense pressure in the tubing 292 and a pressure sensor 284 for sensing pressure in the pressure control valve 280. As shown in FIG. 2C, the tubing 292 is a tube within a tube such that gas supplied from the generator travels to the trocar and patient through tube 296 and gas is released out of the patient through tube 294.

As shown in FIG. 2A the connector 132 to which control module 230 is connected has a gas-enhanced electrosurgical instrument 160 having a connector 162 connected to in. In FIG. 2A, gas control module 230 controls flow of argon gas, so the instrument 160 is an argon gas-enhanced electrosurgical tool such as an argon plasma probe such as is disclosed in U.S. Pat. No. 5,720,745, a hybrid plasma cut accessory such as is disclosed in U.S. Patent Application Publication No. 2017/0312003 or U.S. Patent Application Publication No. 2013/0296846, or a monopolar sealer such as is disclosed in U.S. Patent Application Publication No. 2016/0235462. Other types of argon surgical devices similarly can be used. As shown in FIG. 2B the connector 132 to which control module 240 is connected has a gas-enhanced electrosurgical instrument 170 having a connector 172 connected to in. In FIG. 2B, gas control module 240 controls flow of helium gas, so the instrument 170 is, for example, a cold atmospheric plasma attachment such as is disclosed in U.S. Patent Application Publication No. 2016/0095644.

The system provides for control of intraabdominal pressure in a patient. The pressure control valve 280 has a chamber within it. The pressure in that chamber is measured by pressure sensor 284. $CO_2$ is supplied to the chamber within pressure control valve 280 from gas control module 220 via 3-way proportional valve 260. Pressure in that chamber within the pressure control valve 280 also may be released via 3-way proportional valve 260. In this manner, the system can use the pressure sensor 284 and the 3-way proportional valve to achieve a desired pressure (set through a user interface) in the chamber within the pressure control valve 280. The pressure sensor 282 senses the pressure in the tubing 294 (and hence the intraabdominal pressure). The pressure control valve 280 then releases pressure through its exhaust to synchronize the intraabdominal pressure read by sensor 282 with the pressure in the chamber within the pressure control valve as read by pressure sensor 284. The readings from sensors 282, 284 can be provided to CPU 210, which in turn can control flow of $CO_2$ and one of argon and helium, depending on the procedure being performed, to achieve a stable desired intraabdominal pressure.

Figure 2D:
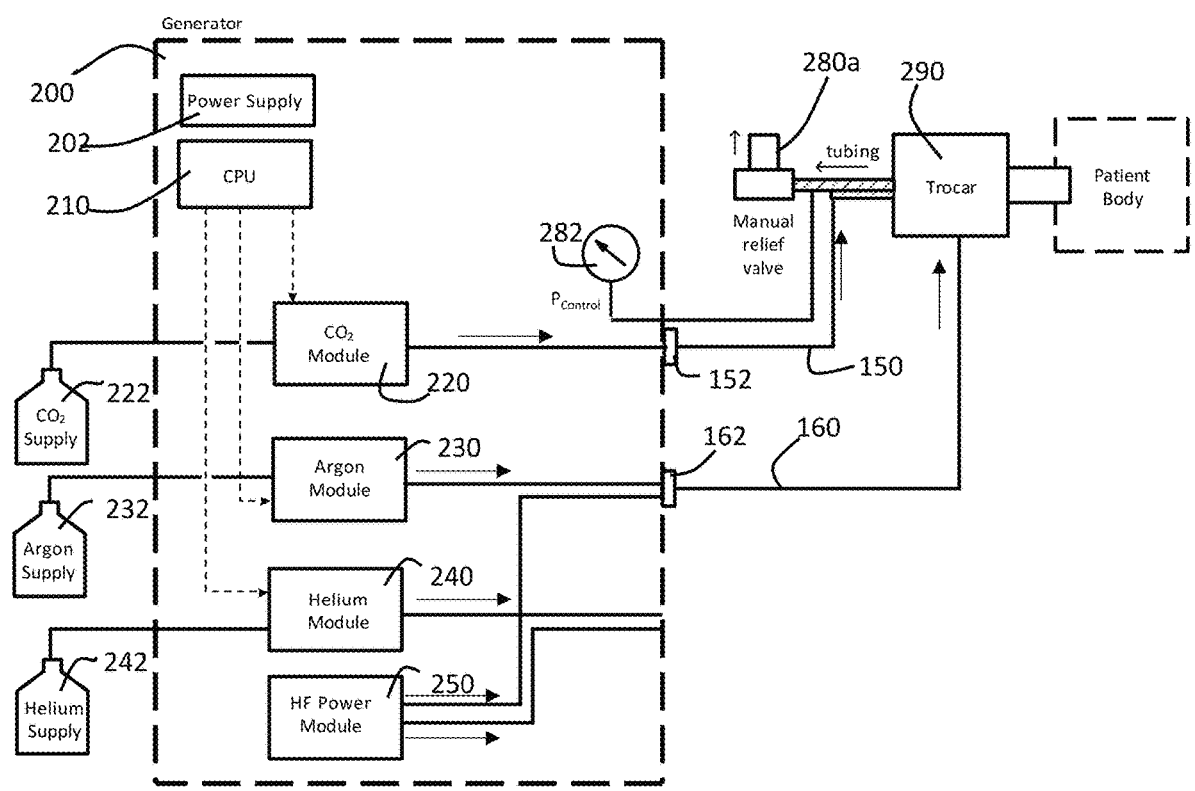
FIG. 2D is a block diagram of an alternate preferred embodiment of pressure control system of a gas-enhanced electrosurgical generator in accordance with the present invention configured to perform an argon-enhanced electrosurgical procedure.

An alternative embodiment of the gas pressure control system is shown in FIG. 2D. This this system the automatic stopcock or pressure control valve 280 has been replaced by a manual relief valve 280a that is controlled or operated by the surgeon using the system.

A gas control module 300 in accordance with the present invention is designed for gas-enhanced electrosurgical systems. Conventionally, gas-enhanced electrosurgical systems have an electrosurgical generator and a gas control unit that have separate housings. The conventional gas control unit typically controls only a single gas such as argon, $CO_2$ or helium. The present invention is a gas control module 300 that may be used in a gas control unit or in a combined unit functioning both as an electrosurgical generator and as a gas control unit. Further, a plurality of gas control modules in accordance with the present invention may be combined in a single gas control unit or combination generator/gas control unit to provide control of multiple gases and provide control for multiple types of gas-enhanced surgery such as argon gas coagulation, hybrid plasma electrosurgical systems and cold atmospheric plasma systems.

FIG. 3A is a schematic flow diagram illustrating the gas flow through the gas control module 300 and the method by which the module 300 controls the gas flow in accordance with a preferred embodiment of the present invention. As shown in FIG. 3A, the gas enters the gas control module at an inlet port (IN) 301 and proceeds to first solenoid valve (SV1) 310, which is an on/off valve. In an exemplary embodiment, the gas enters the gas module at a pressure of 75 psi. The gas then proceeds to a first pressure sensor (P1) 320, to a first pressure regulator (R1) 330. In an exemplary embodiment, the first pressure regulator (R1) 330 reduces the pressor of the gas from 75 psi to 18 psi. After the pressure regulator (R1) 330, the gas proceeds to flow sensor (FS1) 340, which sense the flow rate of the gas. Next, the gas proceeds to proportional valve (PV1) 350, which permits adjustment of a percentage of the opening in the valve. The gas then proceeds to a second flow sensor (FS2) 360, which senses the flow rate of the gas. This second flow sensor (FS2) 360 provides redundancy and thus provides greater safety and accuracy in the system. Next the gas proceeds to a second solenoid valve (SV2) 370, which is a three-way valve that provides for a vent function that can allow gas to exit the module through a vent 372. The gas then proceeds to a second pressure sensor (P2) 380, which provides a redundant pressure sensing function that against produces greater safety and accuracy of the system. Finally, the gas proceeds to a third solenoid valve (SV3) 390, which is a two-way on/off valve that is normally closed and is the final output valve in the module. The gas exits the module at and output port (OUT) 399, which is connected to tubing or other channel that provides a passageway for the gas to flow to an accessory connected to the electrosurgical unit.

FIG. 3B is a schematic flow diagram of an alternate embodiment of a gas control module illustrating the gas flow through the gas control module 300a and the method by which the module 300a controls the gas flow in accordance with a preferred embodiment of the present invention. As shown in FIG. 3B, the gas enters the gas control module at an inlet port 301a and proceeds to a first pressure regulator (R1) 330a. In an exemplary embodiment, the first pressure regulator (R1) 330a reduces the pressor of the gas from about 50-100 psi to 15-25 psi. After the pressure regulator (R1) 330a, the gas proceeds to a first pressure sensor (P1) 320a and then to a first solenoid valve (SV1) 310a, which is an on/off valve. Next, the gas proceeds to proportional valve (PV1) 350a, which permits adjustment of a percentage of the opening in the valve. Next, the gas proceeds to flow sensor (FS1) 340a, which sense the flow rate of the gas. ext the gas proceeds to a second solenoid valve (SV2) 370a, which is a three-way valve that provides for a vent function that can allow gas to exit the module through a vent 372a. The gas then proceeds to a second flow sensor (FS2) 360a, which senses the flow rate of the gas. This second flow sensor (FS2) 360a provides redundancy and thus provides greater safety and accuracy in the system. The gas then proceeds to a second pressure sensor (P2) 380a, which provides a redundant pressure sensing function that against produces greater safety and accuracy of the system. The gas exits the module at and output port 399a, which is connected to tubing or other channel that provides a passageway for the gas to flow to an accessory connected to the electrosurgical unit.

The various valves and sensors in either embodiment of the module are electrically connected to a main PCB Board through a connector 490. The PCB connector 490 is connected to a PCB Board that has a microcontroller (such as CPU 210 in the embodiment shown in FIG. 2A). As previously noted, a plurality of gas modules can be in a single gas control unit or single electrosurgical generator to provide control of multiple differing gases. The plurality of gas control modules further may be connected to the same PCB Board, thus providing common control of the modules.

Figure 4:
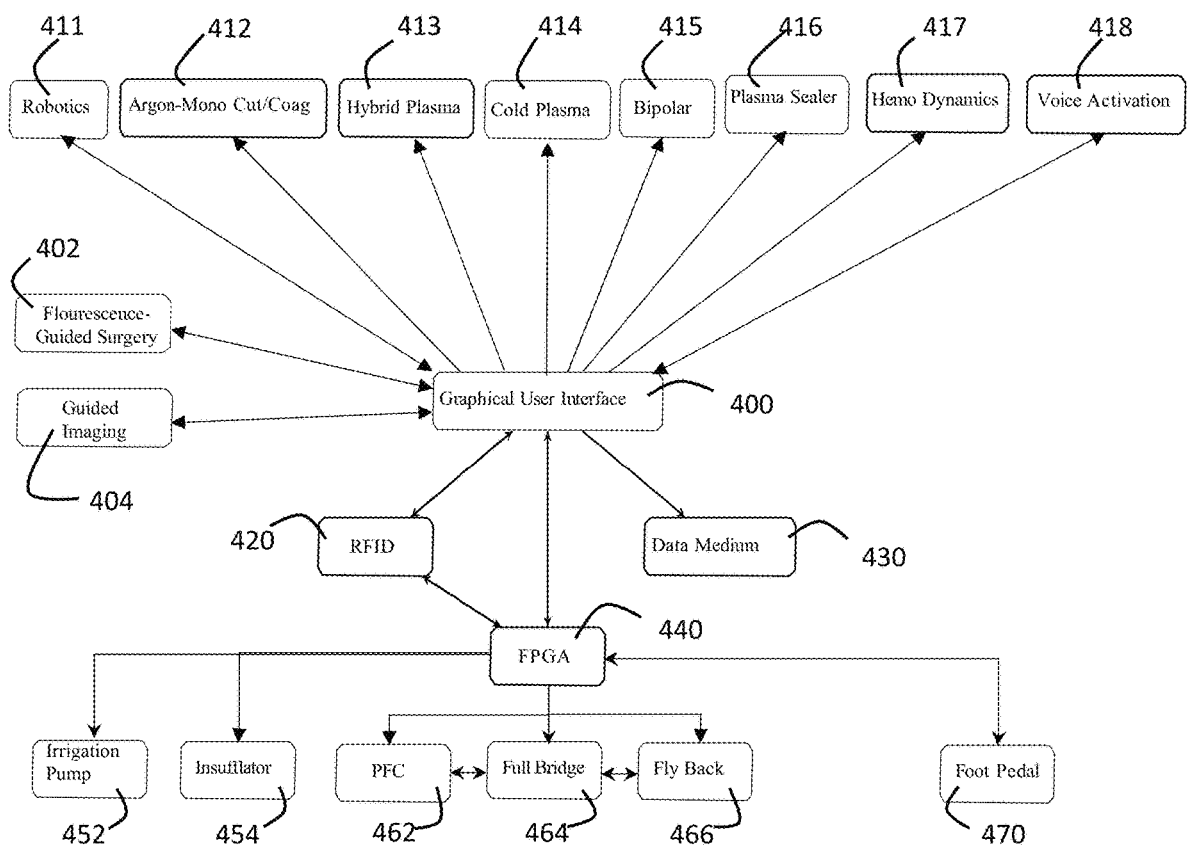
FIG. 4 is a diagram of a graphical user interface in accordance with a preferred embodiment of the present invention.

As shown in FIG. 4, the generator further may have graphical user interface 400 for controlling the components of the system using the touch screen display 120. The graphical user interface 400 for example, may control robotics 411, argon-monopolar cut/coag 412, hybrid plasma cut 413, cold atmospheric plasma 414, bipolar 415, plasma sealer 416, hemo dynamics 417 or voice activation 418. The graphical user interface further may be used with fluorescence-guided surgery 402. For example, J. Elliott, et al., "Review of fluorescence guided surgery visualization and overlay techniques," BIOMEDICAL OPTICS EXPRESS 3765 (2015), outlines five practical suggestions for display orientation, color map, transparency/alpha function, dynamic range compression and color perception check. Another example of a discussion of fluorescence-guided surgery is K. Tipirneni, et al., "Oncologic Procedures Amenable to Fluorescence-guided Surgery," Annals of Surgery, Vo. 266, No. 1, July 2017). The graphical user interface (GUI) further may be used with guided imaging such as CT, MM or ultrasound. The graphical user interface may communicate with RFID 420 (such as may be found in various electrosurgical attachments) and may collect and store usage data in a storage medium 430. The graphical user interface 400 communicates with FPGA 440, which may control irrigation pump 452, insufflator 454, PFC 462, full bridge 464 for adjusting the power output, fly back 466 for regulating the power (DC to AC) and a foot pedal 470. The GUI 400 further communicates with a database of cancer cell line data with associated predicted CAP settings or dosages via the CPU 210. The databases storage may be internal memory or other internal storage 211 or external storage 212 as shown in FIGS. 2A and 2B. The data storage 430 in FIG. 4 may be in one or both memories or storages 211 or 212.

Figure 5A:
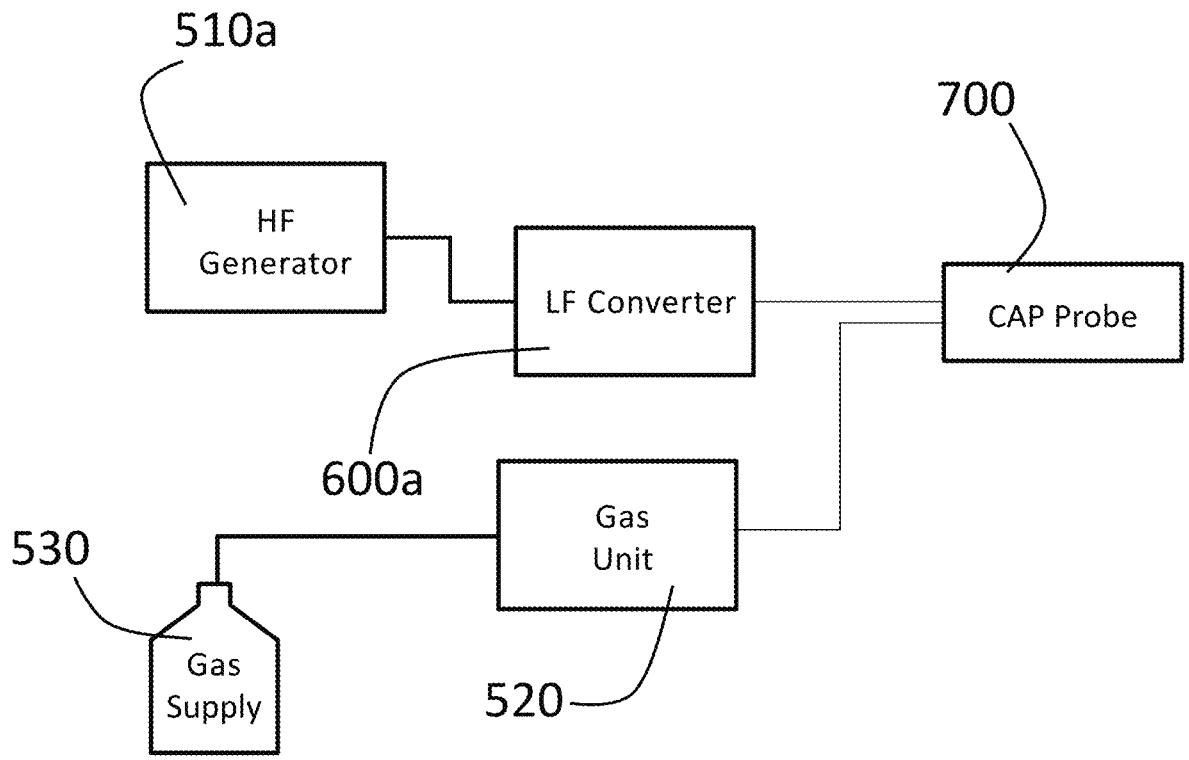
FIG. 5A is a diagram of a first embodiment of a system for producing cold plasma in accordance with the present invention.

A first embodiment of a system for producing cold plasmas is shown in FIG. 5A. The system has a high frequency (HF) electrosurgical generator or ESU, a low frequency (LF) converter 600, a gas unit 520, a gas supply 530 and a cold atmospheric plasma (CAP) probe 700. The CAP probe 700 is connected to an output of the LF power converter 600 and the gas unit 520. The gas supply 530 is a source of an inert gas such as helium. The gas unit 520 controls the flow of the inert gas to the CAP probe 300. The HF electrosurgical generator 510 supplies high frequency (HF) energy for performing electrosurgical procedures such as electrocautery, argon plasma coagulation and others. The HF energy, for example, may have a frequency of 500 kHz, meaning that the generator outputs energy at a range of frequencies centered at 500 kHz. If the generator is set, for example, at a power of 100 W, the 100 W power at the center frequency of 500 kHz will dominate the signal. Power levels at frequencies surrounding that center frequency will be lower the further those surrounding frequencies are from the center frequency. Conventional electrosurgical generators operate in this manner and would be known to those of skill in the art. In conventional electrosurgical generators, the dominant central frequency typically is in the range of 300 kHz-600 kHz. This dominant central frequency sometimes may be referred to as the "rated frequency."

Figure 6:
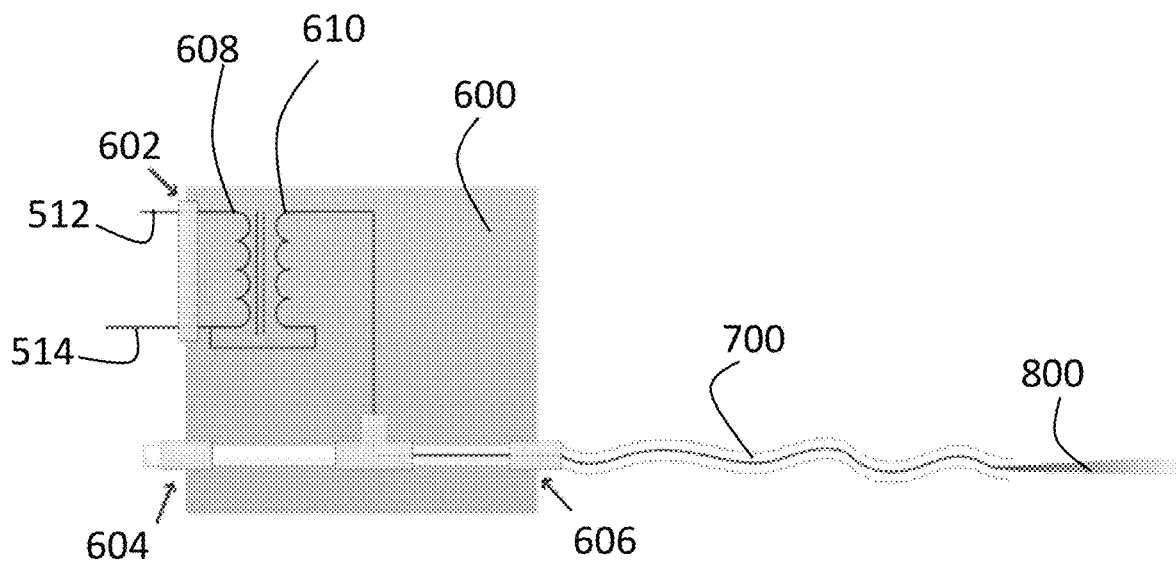
FIG. 6 is a diagram of a low frequency (LF) module and Cold Atmospheric Plasma (CAP) Probe in accordance with a preferred embodiment of the present invention.

The LF converter 600 utilizes a high voltage transformer connected to an output from ESU 510 as shown in FIG. 6. The transformer is a tuned transformer and is tuned to a lower frequency than the central frequency output from the ESU. In other words, the transformer operates as a resonant transformer with a resonant frequency lower than the output frequency of the ESU. For example, if the ESU outputs energy centered at 500 kHz, the transformer may have a resonant frequency of less than 300 kHz.

In a preferred embodiment, the transformer utilizes a primary coil 208 with $N_1$=60-70 turns and secondary coil 610 with about $N_2$=300 turns. The coils are wound on a ferrite core. The specific number of turns utilized in the transformer is given for illustrative purpose only and can be varied in a very wide range. The number $N_2$ should be larger than $N_1$ in order to produce step-up conversion of the voltage.

EXAMPLES

Cell Culture, Treatment and Viability Assay

Human breast cancer cells were cultured in DMEM supplemented with 10% fetal bovine serum and 1% Pen Strep in a 37° C. and 5% $CO_2$ humidified incubator. When cells reached approximately 80% confluence, cells were seeded at a concentration of $10^5$ cells/well into 12-well plates (USA Scientific, Ocala, Fla.) or $5\times10^3$ cells/well into 96-well plates (USA Scientific, Ocala, Fla.). Helium flow was set to a constant 1 lpm at power set 20 P or 40 P on the USMI SS-601 MCa or 3 lpm and power set to 40 P, 60 P, or 80 P. The plasma scalpel was placed 1.5 cm (at 1 lpm) or 2 cm (at 3 lpm) away from the surface of the cell media. Well-plates were placed on a plate heater (Benchmark, New York, N.Y.) which maintained temperature at 37° C., providing a relatively warmer and gentle environment for the cells during treatment. Thiazolyl Blue Tetrazolium Bromide (MTT) assay was performed on the cells 48 hr after plasma treatment following the manufacturer's protocol. All the MTT assay reagents were purchased from Sigma-Aldrich (St. Louis, Mo.). The absorbance of the dissolved compound was measured by BioTek Synergy HTX (Winooski, Vt.) microplate reader at 570 nm.

Cold Plasma Device Power and Temperature Measurement

Electric parameters of the cold plasma discharge were measured using Tektronix P6021A (Tektronix, Beaverton, Oreg.) current probe with a frequency range of 120 Hz to 60 MHz and PPE 6 kV high voltage probe (LeCroy, Chestnut Ridge, N.Y.) attached to a digital oscilloscope Wavesurfer 3024 (LeCroy, Chestnut Ridge, N.Y.). Helium flow rates at 1 lpm and 3 lpm were measured at different power settings. A thermal camera (FLIR E4) was used to collect temperature data. The volume of the media in each well was 1 ml for 12-well plate and 0.1 ml for 96-well plate. The distance between the tip of the scalpel and the surface of the media was kept at 1.5 cm (at 1 lpm) or 2 cm (at 3 lpm). Temperature measurement of the CAP-treated media was also performed with the plate heater set to 37° C., which was consistent with cell viability experiments. The temperature of the beam and treated media was measured every minute from 0 min (immediately after the CAP was on) to 5 min.

Statistics

All viability assays were repeated for at least 3 times with 3 replicates each time. Data was plotted by Microsoft Excel 2016 as mean±standard error of the mean. Student t-test or one-way analysis of variance (ANOVA) were used to check statistical significance where applicable. Differences were considered statistically significant for * $p<0.05$.

Results

Figure 5B:
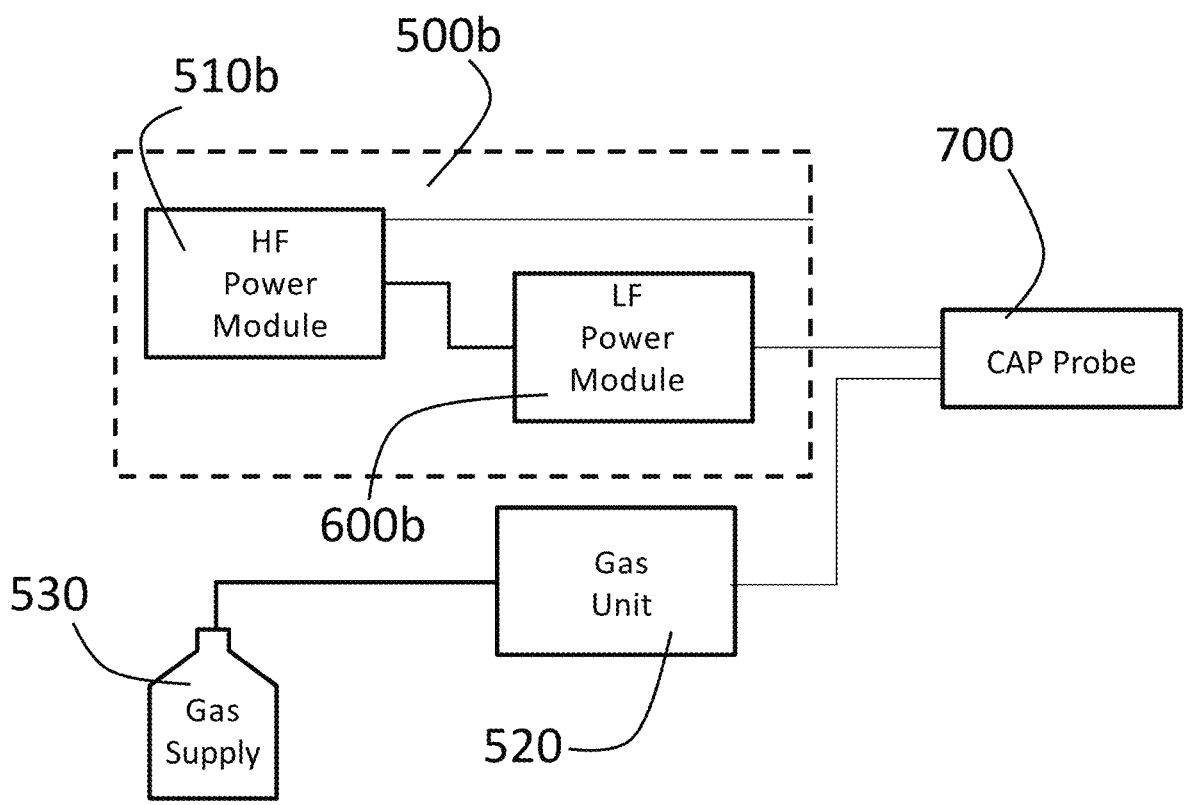
FIG. 5B is a diagram of a second embodiment of a system for producing cold plasma in accordance with the present invention.
Figure 5C:
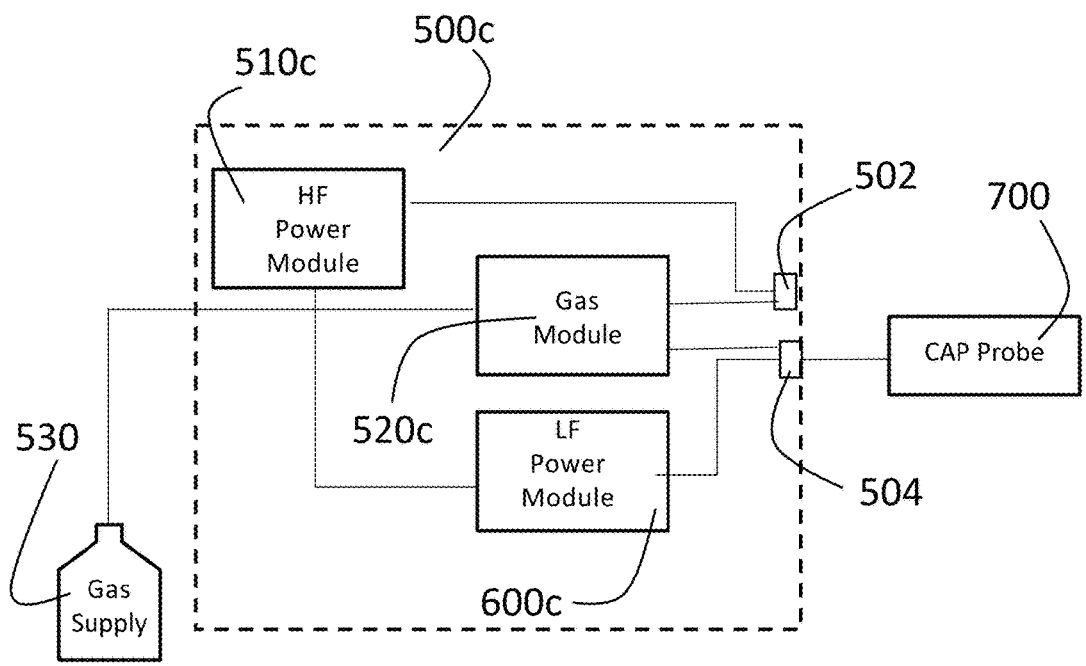
FIG. 5C is a diagram of a third embodiment of a system for producing cold plasma in accordance with the present invention.

The system used in the examples is comprised of two units, namely the conversion unit (CU) and the cold plasma probe (CPP). The CU is integrated with a USMI SS-601 MCa, a high-frequency electrosurgical generator (ESU) unit and converts the ESU signal. The CPP is connected to the CU output. Plasma is produced at the end of the CPP and is thermally harmless to living tissue, i.e. it is cold plasma. The connection schematics are shown in FIG. 5A. The CU is equipped with 3 connectors, namely a gas connector (to a helium tank), an electrical connector (to ESU) and an electro-gas connector (to CPP). The CU utilizes a high voltage transformer connected to the output from the ESU. The CU up-converts voltage up to 4 kV, down-converts frequency to less than 300 kHz, and down-converts power to less than 40 W. The CPP is connected to an electro-gas output connector of the CU and has a length of 0.5 m. FIGS. 5B and 5C show alternate arrangements using an LF converter box.

Power and Temperature Measurement of CAP

Figure 7A:
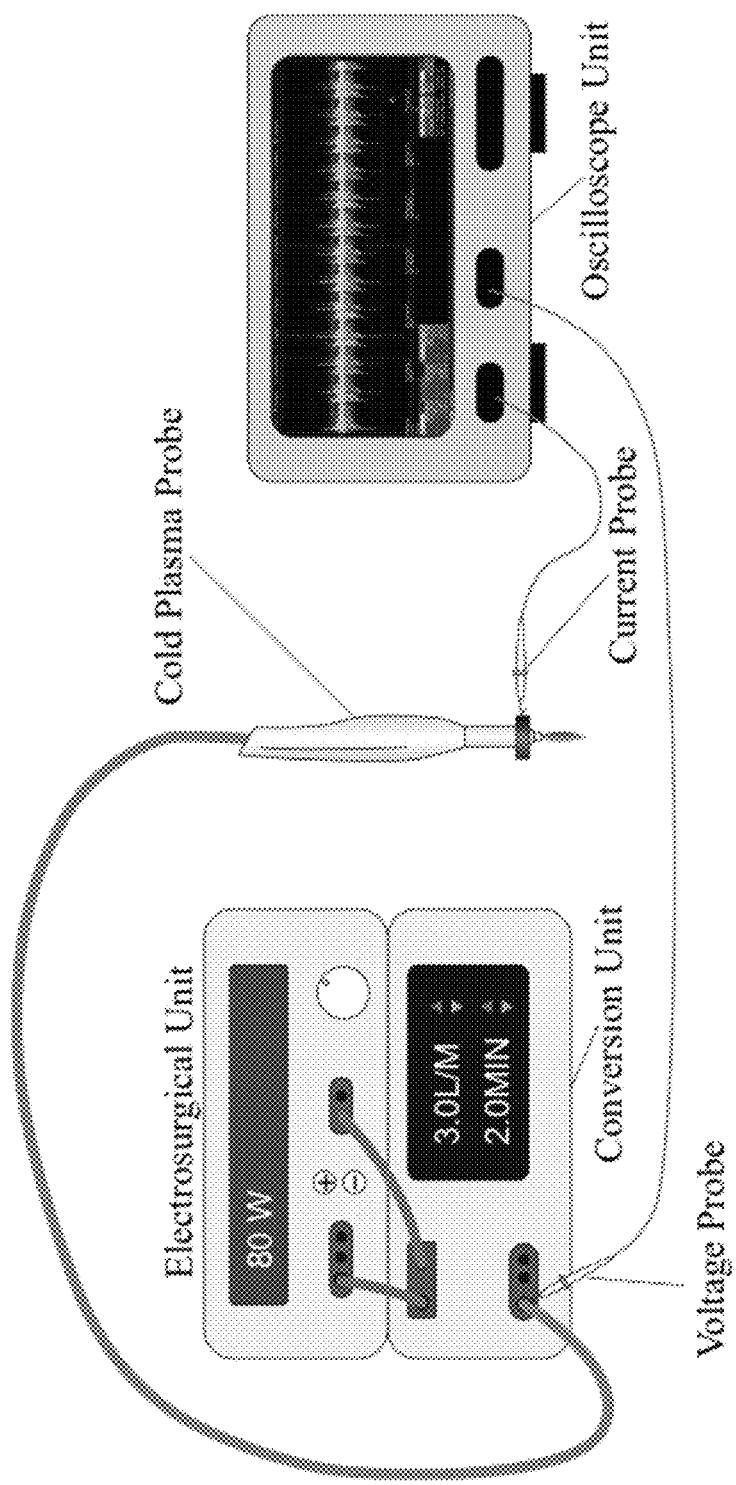
FIG. 7A is a schematic image of power testing setup.
Figure 7B:
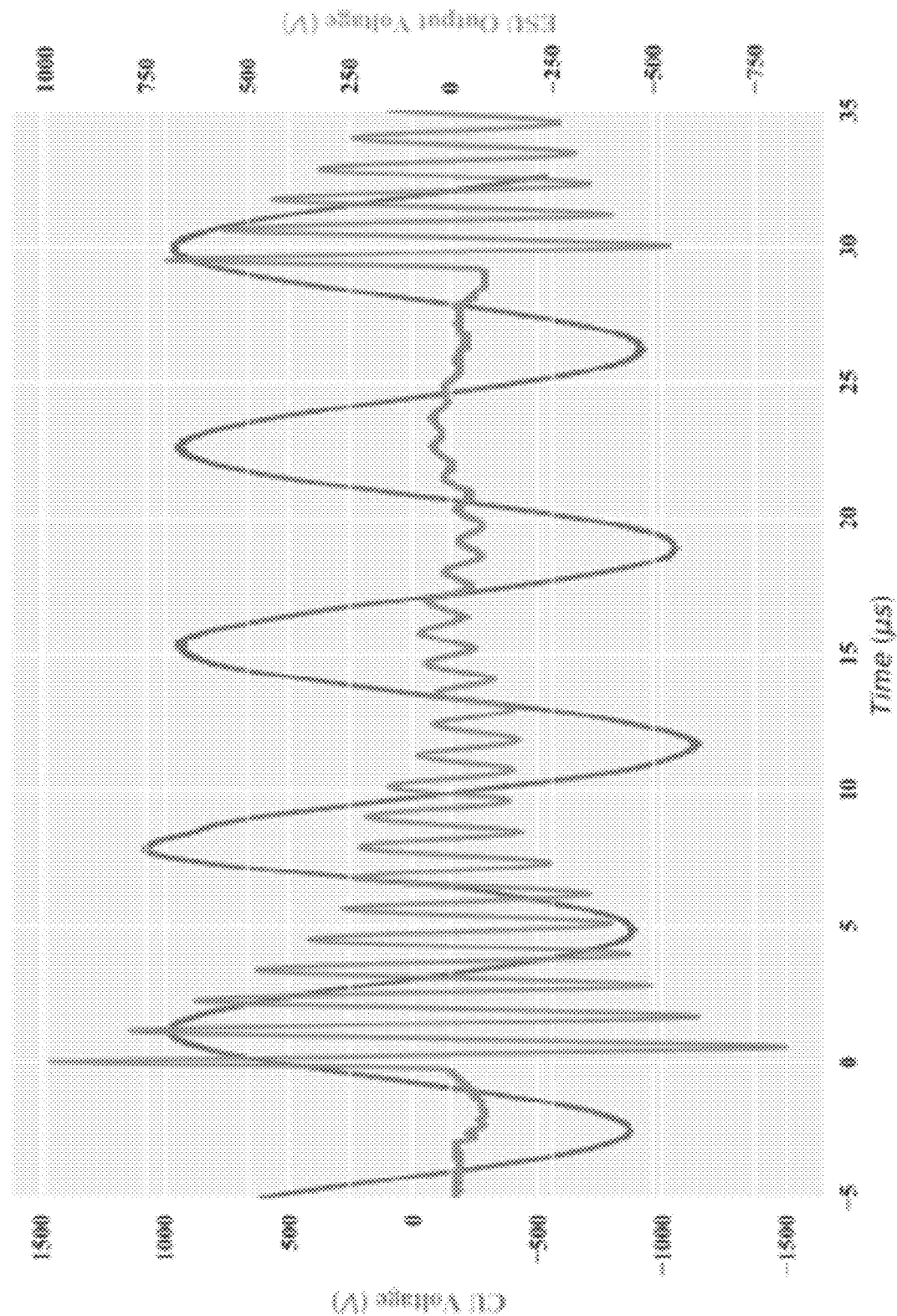
FIG. 7B is a graph of output voltage of the ESU and the CU measured across the plasma scalpel tip.

The electric parameters of the cold plasma discharge were measured and a schematic image of the setup is shown in FIG. 7A. FIG. 7B shows the output voltage of the ESU (orange line) and the CU (blue line). The ESU spray mode is a pulse modulated system. The ESU generated series of high voltage bursts with peak amplitude of about 1 kV separated about 30 µs between the bursts. Each voltage burst was filled with harmonic oscillations at a frequency of about 880 kHz. The CU output waveform had a smaller resonate frequency about 140 kHz and amplitude about 1-1.5 kV. That is to say, the CU is not a power generating device, but a frequency and voltage modulation device.

Figure 7C:
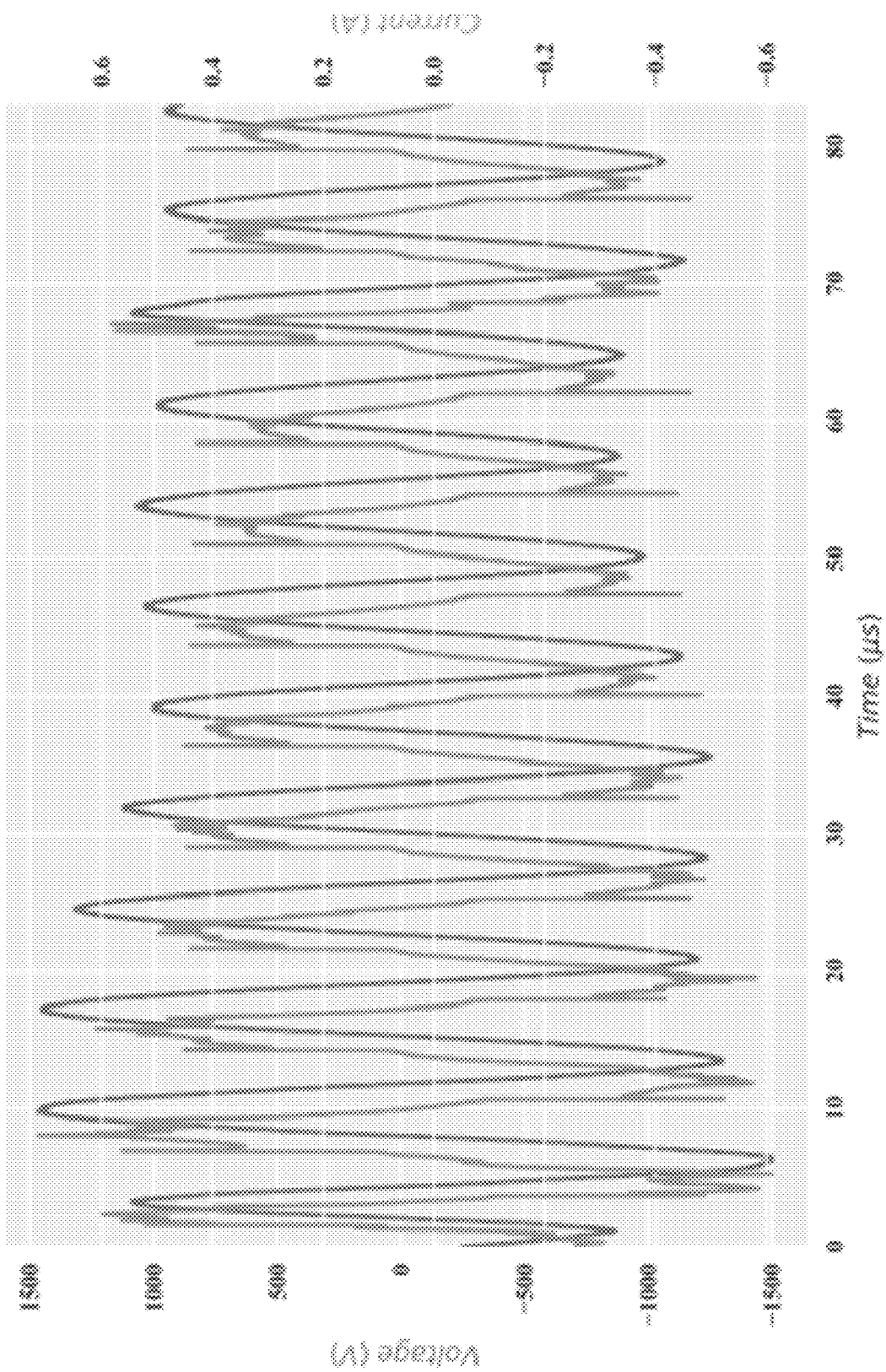
FIG. 7C is a graph of output voltage and current signals from the CU.

The output voltage and current signals from the CU using 3 lpm are shown in FIG. 7C. The blue line indicates the voltage output from the CU and the orange line is the current dissipate through the CPP, with the ESU set to 60 P. We observed a phase shift between voltage and current curve; the current curve is about 80 degrees ahead of the voltage curve. In other words, the cold plasma system is acting as neither a pure resistive nor a pure reactive impedance. Therefore, the real power delivered to the discharge was calculated as follows. The power deposited into the cold plasma discharge was calculated by the oscilloscope directly as $1/T\int_T U \cdot I \, dt$ for large integration time T=2 ms (over 20M data points, more than 200 oscillations). The power deposited into the cold plasma discharge at 20 P, 40 P, 60 P, 80 P, 100 P, and 120 P for 3 lpm and 1 lpm was plotted in FIG. 7D. The power settings of 20 P, 40 P, 60 P, 80 P, 100 P, and 120 P yield powers deposited into the cold plasma discharge of 5 W, 8 W, 11 W, 15.7 W, 22.3 W, and 28.7 W at 3 lpm respectively; 5 W, 6 W, 7 W, 8 W, 9 W, and 11 W at 1 lpm respectively.

Figure 7E:
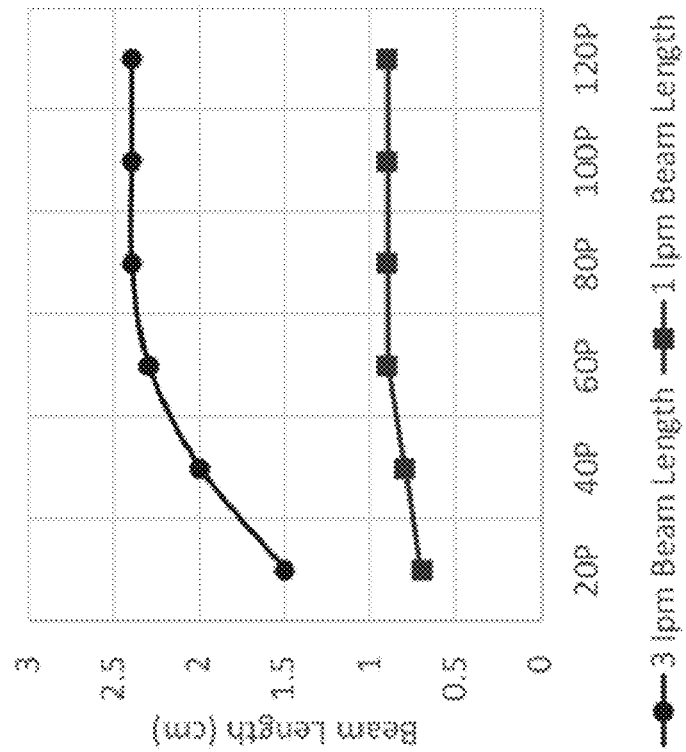
FIG. 7E is a graph of beam length of the CAP jet.
Figure 7D:
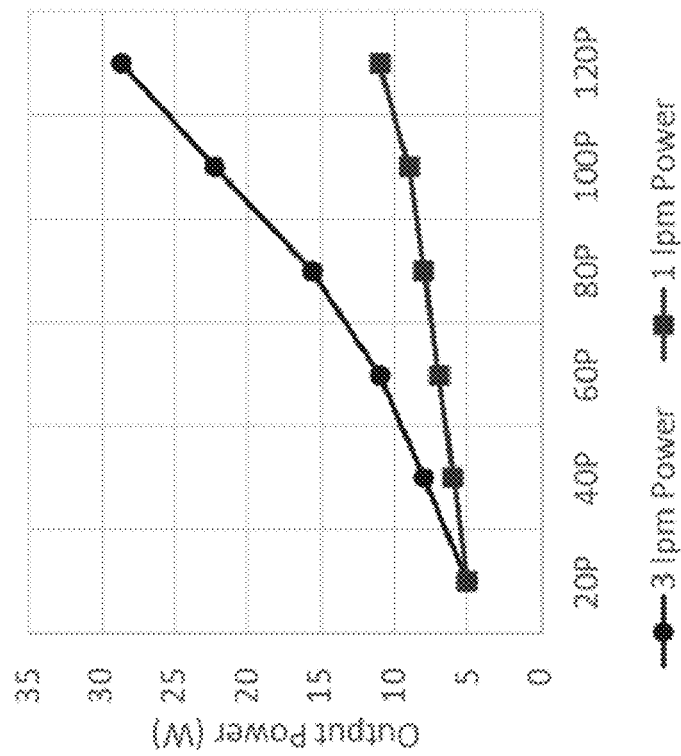
FIG. 7D is a graph of power measurement of the CU.

The length of the CAP beam was also measured at different power settings for both flow rates and plotted in FIG. 7E. At 3 lpm, the length of the beam increases rapidly from 1.5 cm to 2 cm and to 2.3 cm when the power is increased from 20 P to 40 P and to 60 P. After 60 P, the length remains constant at 2.4 cm as the power further increases up to 120 P. This trend also applies to 1 lpm. The length of the beam increases from 0.7 cm to 0.8 cm when the power increases from 20 P to 40 P, and maintains a length of 0.9 cm for 80 P, 100 P, and 120 P.

Figure 8A:
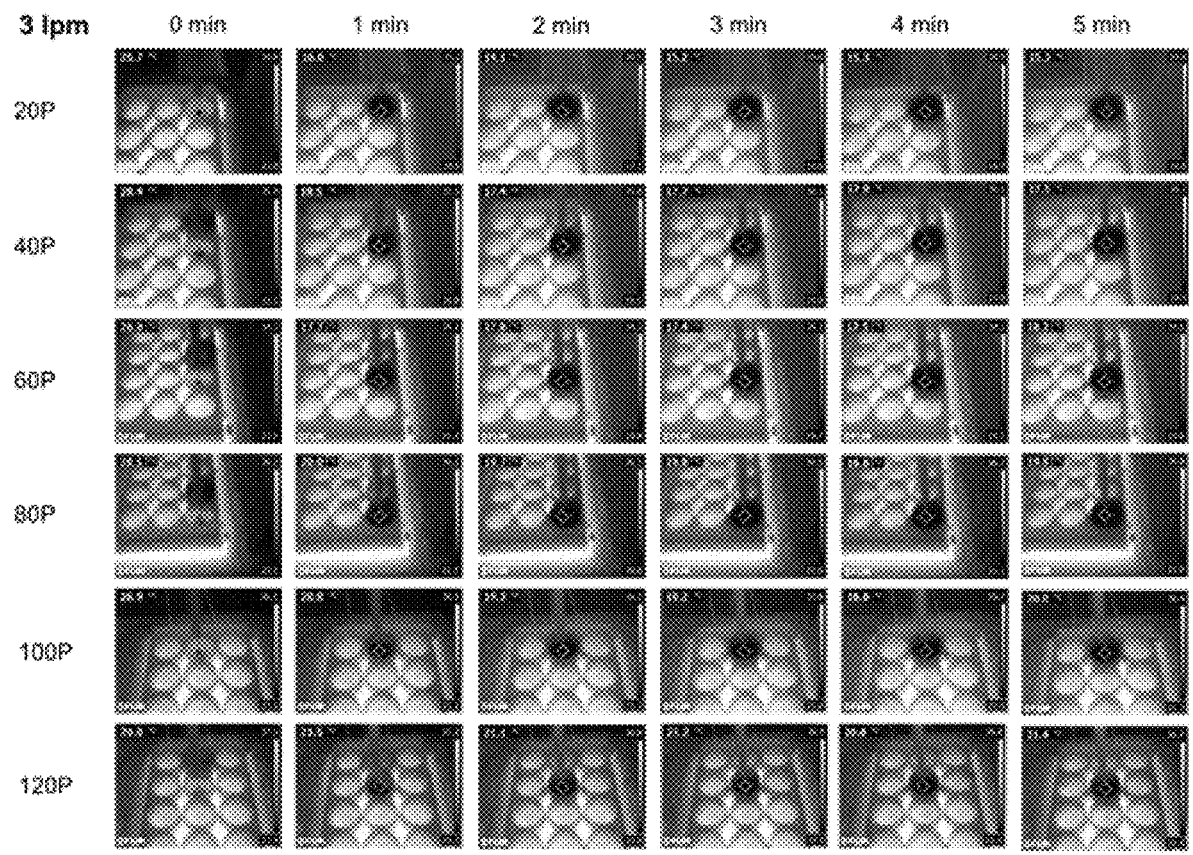
FIGS. 8A-8C illustrate temperature measurements at flow rate of 3 lpm for each power setting.
Figure 8B:
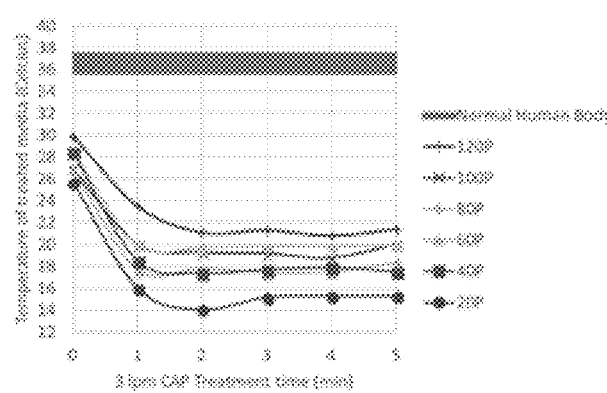
Figure 8C:
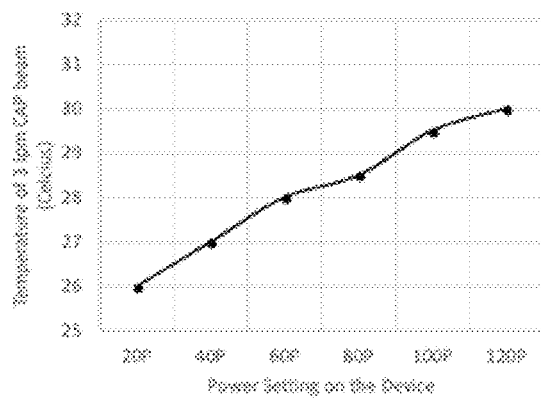
Figure 9A:
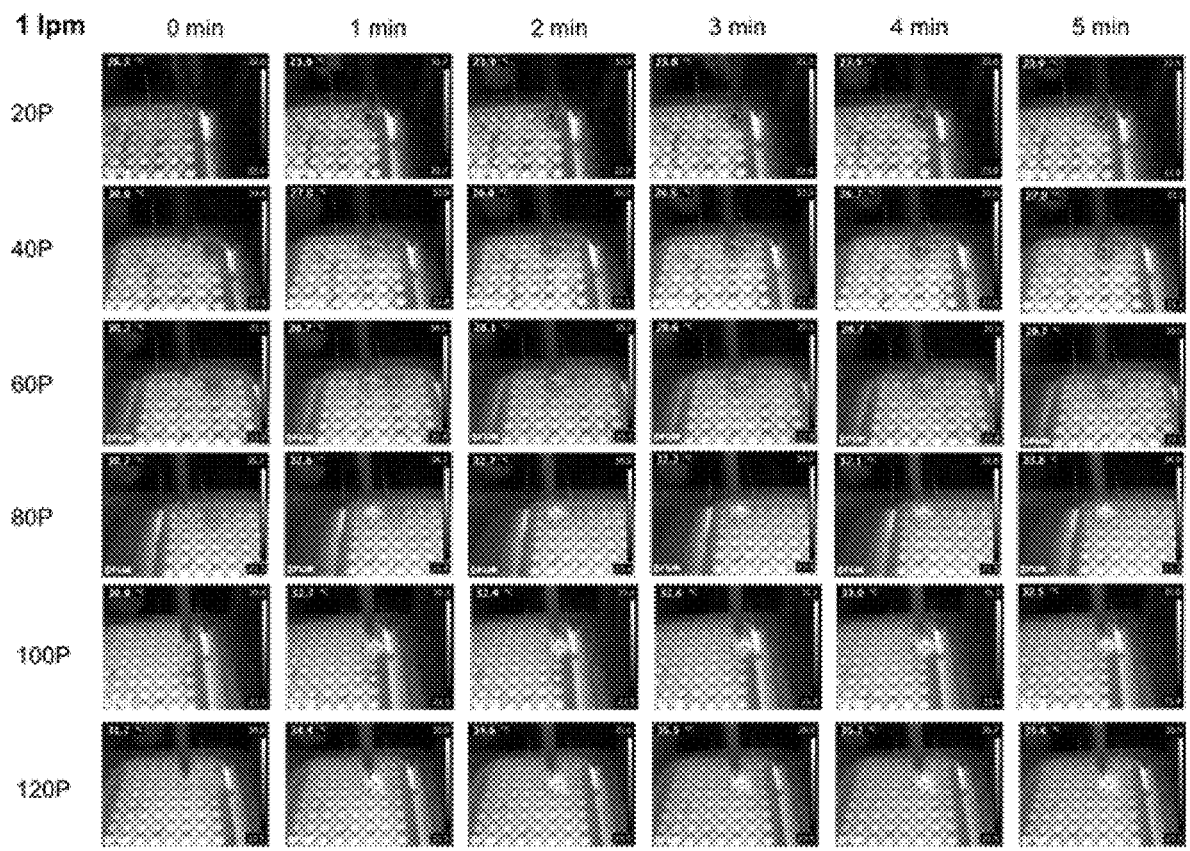
FIGS. 9A-9C illustrate temperature measurements at flow rate of 1 lpm for each power setting.
Figure 9B:
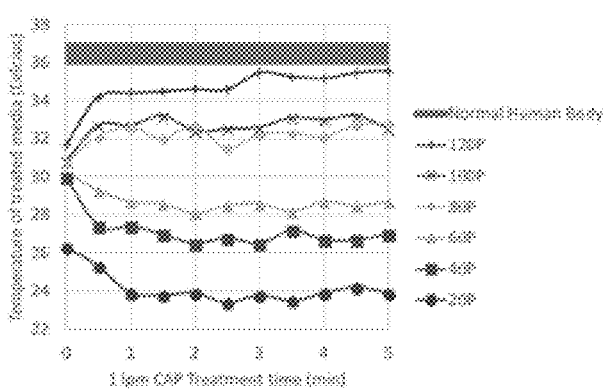
Figure 9C:
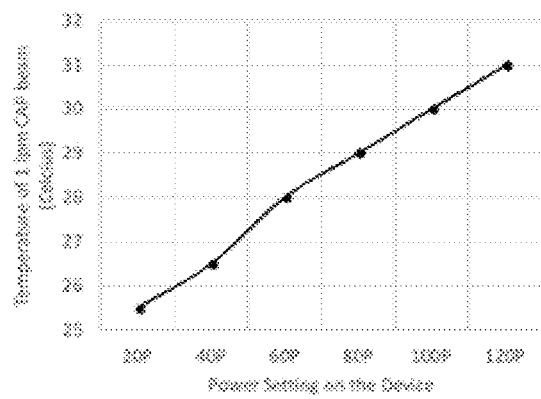

Thermal images of the CAP jet with flow rates of 3 lpm and 1 lpm are shown in FIG. 8A and FIG. 9A respectively. Cell culture media was warmed up to 37° C. beforehand and added to well plates immediately before measurement. The environment temperature was about 23° C. during the experiment. As shown in the graphs, for both flow rates the temperature of the treated media (FIG. 8B and FIG. 9B) as well as the CAP beam (FIG. 8C and FIG. 9C) increases with power increasing from 20 P to 120 P. The beam temperature of 3 lpm CAP is about 26 to 30° C., whereas the treated area of the 12-well plate is 15 to 21° C. In the case of 1 lpm, the beam temperature is in the range of 25.5 to 31° C., and the treatment area is roughly 23 to 36° C.

Cell Viability after CAP Treatment

Figure 10A:
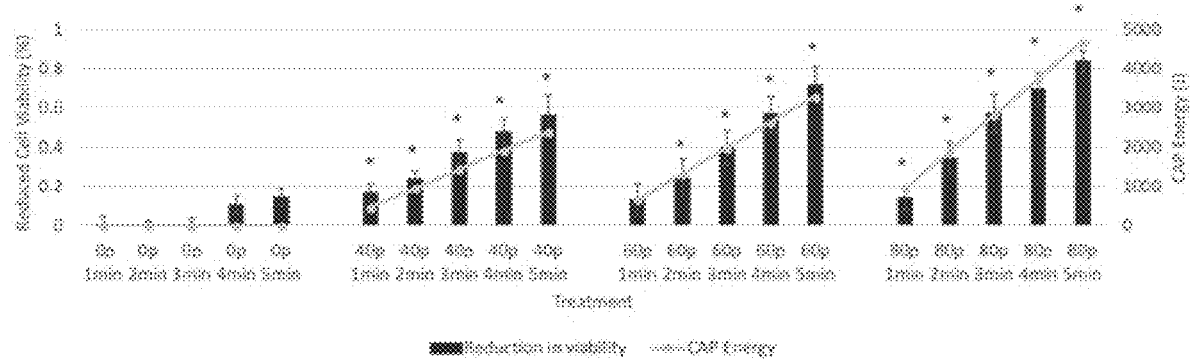
FIGS. 10A and 10B are graphs illustrating reduced viability of treatment on MDA-MB-231 measured by MTT assay (bar chart, primary axis) and energy deposited in the corresponding CAP treatment (line chart, secondary axis).
Figure 10B:
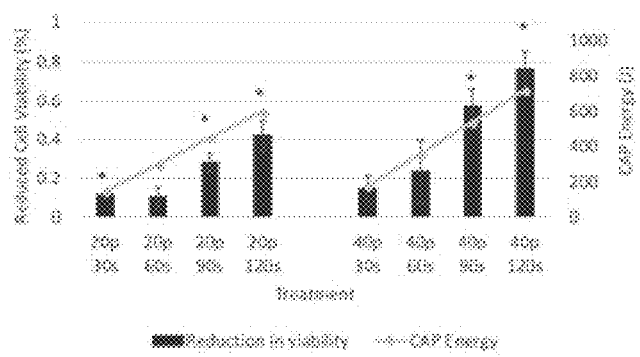

Cells were treated by the Canady Cold Plasma Conversion System and viability was quantified by MTT assay 48 hours after CAP treatment. As shown in FIGS. 10A and 10B primary axis, CAP treatment significantly reduced the proliferation of triple-negative cancer cells at various conditions. CAP treatment of MDA-MB-231 significantly reduces viability at nearly all doses tested using 3 lpm (FIG. 10A). At 1 lpm flow rate, higher treatment times (90 s-120 s) were needed to reduce viability (FIG. 10B).

The energy delivered by the CU to the CPP can be calculated as $$E = P*t$$

where E is the total energy of the CAP (J) delivered by the system; P is the power measured at the end of the CPP (W), and t is the treatment time (s). The consumed energy of each CAP treatment condition used in this study was plotted as the secondary axis of FIGS. 6A (3 lpm) and 6B (1 lpm). The reduction of cell viability matches the energy consumption for both flow rates and this trend is consistent across all power and time settings tested.

DISCUSSION

Cold plasma can be generated in various forms including dielectric barrier discharge, corona discharge, and plasma jets. The Canady Cold Plasma Conversion Unit reported in this study is the first cold plasma device that utilizes a high voltage transformer to up-convert the voltage, down-convert the frequency, and down-convert the power of the high voltage output from an electrosurgical unit (U.S. Pat. No. 9,999,462).

The plasma jet generated by the Canady Cold Plasma Conversion System is indeed "cold". The beam temperature for all conditions tested is within the range of 26 to 31° C. It has a cooling effect on the treated media when the flow rate is high and/or power is low. With a flow rate at 3 lpm, the beam temperature is 26 to 30° C. for 20 P to 120 P, whereas the treated media in the 12-well plate is about 15 to 21° C. respectively.

The beam temperature of 1 lpm CAP is 25.5 to 31° C. for 20 P to 120 P, which is very close to that of 3 lpm. Although the power parameters of CAP are higher at 3 lpm than 1 lpm, as shown above in the Results Section, the similar temperature could be resulted from better heat convection of the higher flow. For a lower power setting of 20 P to 60 P, the temperature of the CAP-treated media in the 96-well plate at 1 lpm, 24 to 29° C., is lower or close to the CAP beam temperature. However, for the higher power setting of 80 P to 120 P, the temperature of the treated media in the 96-well plate, 32 to 36° C., is 3 to 5 degrees higher than the beam temperature. Theoretically, the media temperature should only increase to the beam temperature based on the principle of heat transfer. However, during the experiments we observed that the CAP jet was intensified, which could be caused by the energy dissipating to the wall of the 96-well plate due to the high power as well as the turbulence resulting from a small well size. The increased intensity of the CAP jet is demonstrated as high brightness in the thermal images in FIG. 9A Row 4 to Row 6 (80 P to 120 P). The length of the CAP beam also presents evidence of increased intensity. As shown above in FIG. 3C, the beam is only 0.9 cm at 80 P to 120 P for 1 lpm when measured in open air, while the thermal images in FIG. 9A were captured with 1.5 cm gap distance between the CPP tip and the media. This disparity is because when treating in the well, even at lower power settings, the beam is able to reach 1.5 cm and contact the media. The 3 lpm CAP jet does not present this issue because the diameter of a 12-well plate is significantly larger than the CAP jet.

When applied to cells, power settings of 20 P to 80 P for 3 lpm and 20 P to 40 P for 1 lpm were chosen to ensure the integrity of the CAP delivered to the cells. The temperature of the treatment area is between 15 to 30° C. for all treatment conditions at all times, suggesting no thermal damage to the cells.

The CAP generated by the Canady Cold Plasma Conversion System affects triple-negative breast cancer in a power- and time-dependent manner which corresponds with the increased output power and beam length shown in FIG. 7C. The CAP reduced the viability of triple-negative breast cancer up to 80% at the highest power for both flow rates. To further illustrate the correspondence between cell viability and CAP power and treatment time, we calculate the energy delivered by the system; E. The close correlation between energy consumption and reduction in viability may be important for comparing results between different CAP devices. Difference cancer types may also respond differently to CAP treatment, therefore future studies of other cell lines are required to confirm the liner correlation. Animal studies are needed to determine the optimal dosage for cancer elimination while remaining safe for normal tissue.

Although at 3 lpm, the CAP jet delivers higher energy than 1 lpm with the same power and time setting, the MTT assay shows a similar reduction in viability (FIGS. 10A and 10B). Thus, direct comparison of the cell viability cannot be made between 3 lpm and 1 lpm despite the same power setting and treatment time due to different beam length, well size, medium volume, and cell number between the two conditions.

Figure 11:
FIG. 11 is a graph illustrating reduction rate of MDA-MB-231 cells by CAP treatment under different conditions.

To better understand the strength of each cold plasma dosage and evaluate the efficiency of the cold plasma beam during treatment, Cell Viability Reduction Rate (CVRR) is introduced. CVRR was calculated based on the cell viability rate versus the time at a constant ESU power setting. FIG. 11 shows the CVRR values and averaged CVRR corresponding to 40 P, 60 P and 80 P ESU power setting. There is little difference when comparing the CVRR between treatment times and the average only increases slightly with increased power. In other words, the average CVRR value could represent the overall performance of the CAP for that power setting. More importantly, one could establish a treatment projected solution based on the average CVRR value, and in that sense, CVRR is an ideal parameter to calculate the CAP dose.

The poor prognosis and low overall survival rate of triple negative breast cancer demands a novel and safe treatment. The high-frequency converted cold plasma system integrates coagulation and CAP in a single device, making it more practical for medical applications. After the surgeon removes the cancerous tumor, CAP is subsequently sprayed at the surgical margins to ablate any remaining cancerous tissue or cells, thus reducing the chances of cancer recurrence. CAP treatment acts as an important adjunct to the current treatment protocol for solid cancerous tumors. This new plasma system will change the landscape of electrosurgery and cancer therapy as well as offer cancer patients new hope in the very near-future.

A first cold plasma jet was delivered and was characterized and tested on triple negative breast cancer cells. Viability of these cells was effectively reduced in a time- and power-dependent manner. The present system and method allow for the treatment of surgical margins following the removal of a tumor and for ablating cancer cells using a single device, and this study will contribute to the dosage estimation for patients in future clinical applications.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for performing cold atmospheric plasma therapy to treat cancer in a patient, the method comprising:
    sampling a cancerous tumor in the patient;
    performing cold atmospheric plasma treatment at a plurality of settings on sampled cancerous tumor cells ex vivo;
    storing said settings and results of said ex vivo cold atmospheric plasma treatment in an electronic storage media;
    calculating from said stored settings and results with a processor a cell viability reduction rate of each of a plurality of tested samples;
    calculating from said calculated cell viability reduction rates with a processor an average cell viability reduction rate;
    projecting cold atmospheric plasma dosages to be used in treatment of the cancerous tumor in vivo based upon said calculated average cell viability reduction rate;
    surgically removing the tumor from the patient; and
    treating the surgical margins of the tumor in the patient with cold atmospheric plasma at the projected dosages.

2. A method for performing cold atmospheric plasma therapy to treat cancer according to claim 1 wherein the cancer comprises breast cancer.

* * * * *